United States Patent
Kong et al.

(10) Patent No.: US 11,401,620 B2
(45) Date of Patent: Aug. 2, 2022

(54) METHOD OF PRODUCING PATTERNED MICROWIRE BUNDLES

(71) Applicants: Paradromics, Inc., Austin, TX (US); The Board Of Trustees Of The Leland Stanford Junior University, Stanford, CA (US)

(72) Inventors: Yifan Kong, Austin, TX (US); Matthew R. Angle, Austin, TX (US); Mina-Elraheb Hanna, Palo Alto, CA (US); Abdulmalik Obaid, Palo Alto, CA (US); Nicholas Melosh, Menlo Park, CA (US)

(73) Assignees: PARADROMICS, INC., Austin, TX (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 393 days.

(21) Appl. No.: 16/584,630

(22) Filed: Sep. 26, 2019

(65) Prior Publication Data

US 2020/0056299 A1 Feb. 20, 2020

Related U.S. Application Data

(63) Continuation of application No. PCT/US2018/025576, filed on Mar. 30, 2018.
(Continued)

(51) Int. Cl.
*H01R 43/00* (2006.01)
*C25D 7/06* (2006.01)
(Continued)

(52) U.S. Cl.
CPC .......... *C25D 7/0607* (2013.01); *A61N 1/0529* (2013.01); *A61N 1/37205* (2013.01); *Y10T 29/49117* (2015.01)

(58) Field of Classification Search
CPC ..... A61B 2017/00526; A61F 2002/016; Y10T 29/532; Y10T 29/49117; A61N 1/0529; A61N 1/0551
(Continued)

(56) References Cited

U.S. PATENT DOCUMENTS 3,982,529 A 9/1976 Sato
5,008,733 A 4/1991 Mine et al.
(Continued)

FOREIGN PATENT DOCUMENTS

EP 2495011 A1 9/2012
WO WO-2017180482 A1 10/2017
WO WO-2018183967 A1 10/2018

OTHER PUBLICATIONS

Angle et al. Neuronal Recordings with Solid-Conductor Intracellular Nanoelectrodes (SCINEs). PLOS ONE 7(8):E43194 (Aug. 2012). 8 pages.
(Continued)

*Primary Examiner* — Thiem D Phan
(74) *Attorney, Agent, or Firm* — Wilson Sonsini Goodrich & Rosati

(57) ABSTRACT

Systems and methods for manufacturing and processing microwires for use as microelectrodes are disclosed. The disclosed techniques provide methods for creating microelectrode bundles with different organizations and patterns. Systems and methods of the present disclosure also provide methods for electrochemically modifying bundles of microelectrode ends.

7 Claims, 19 Drawing Sheets

Related U.S. Application Data

(60) Provisional application No. 62/479,291, filed on Mar. 30, 2017.

(51) Int. Cl.
*A61N 1/05* (2006.01)
*A61N 1/372* (2006.01)

(58) Field of Classification Search
USPC .............. 29/825, 599, 745, 6, 746, 850, 868
See application file for complete search history.

(56) References Cited

U.S. PATENT DOCUMENTS

| | | | |
|---|---|---|---|
| 5,721,450 | A | 2/1998 | Miles |
| 5,814,122 | A * | 9/1998 | Huang ............... C03B 37/022 65/444 |
| 6,049,038 | A | 4/2000 | Suzuki |
| 6,393,327 | B1 | 5/2002 | Scribner |
| 6,647,297 | B2 | 11/2003 | Scribner et al. |
| 6,815,258 | B2 | 11/2004 | Vincent |
| 6,920,359 | B2 | 7/2005 | Meadows et al. |
| 6,940,182 | B2 | 9/2005 | Hilton et al. |
| 7,091,060 | B2 | 8/2006 | Bolken et al. |
| 7,134,198 | B2 | 11/2006 | Nakatani et al. |
| 7,306,976 | B2 | 12/2007 | Feustel et al. |
| 7,991,475 | B1 | 8/2011 | Tang et al. |
| 8,010,208 | B2 | 8/2011 | Nimer et al. |
| 8,024,049 | B1 | 9/2011 | Gilson et al. |
| 8,280,516 | B2 | 10/2012 | Graupe |
| 8,406,889 | B2 | 3/2013 | Llinas et al. |
| 8,412,332 | B2 | 4/2013 | Massoud-Ansari et al. |
| 8,649,873 | B2 | 2/2014 | Moffitt et al. |
| 8,798,737 | B2 | 8/2014 | Merz et al. |
| 8,849,408 | B1 | 9/2014 | Gilson et al. |
| 8,929,992 | B2 | 1/2015 | Toader et al. |
| 8,944,985 | B2 | 2/2015 | Bonmassar et al. |
| 10,327,655 | B2 | 6/2019 | Angle et al. |
| 2002/0014688 | A1 | 2/2002 | Ramalingam et al. |
| 2004/0006264 | A1 | 1/2004 | Mojarradi et al. |
| 2004/0026792 | A1 | 2/2004 | Vincent |
| 2004/0133118 | A1 | 7/2004 | Llinas |
| 2004/0222010 | A1 | 11/2004 | Tonucci et al. |
| 2005/0217796 | A1 | 10/2005 | Carter et al. |
| 2005/0267347 | A1 | 12/2005 | Oster |
| 2006/0206161 | A1 | 9/2006 | Nicolelis et al. |
| 2006/0265039 | A1 | 11/2006 | Bartic et al. |
| 2007/0106143 | A1 | 5/2007 | Flaherty |
| 2007/0142872 | A1 | 6/2007 | Mickle et al. |
| 2008/0170819 | A1 | 7/2008 | Kodama et al. |
| 2008/0205829 | A1 | 8/2008 | Jacobsen et al. |
| 2008/0208283 | A1 | 8/2008 | Vetter et al. |
| 2009/0004471 | A1 | 1/2009 | Amthor |
| 2009/0120216 | A1 | 5/2009 | Chiou et al. |
| 2010/0029148 | A1 | 2/2010 | Perlin et al. |
| 2010/0114272 | A1 | 5/2010 | Haidarliu et al. |
| 2010/0161019 | A1 | 6/2010 | Clark et al. |
| 2011/0208031 | A1 | 8/2011 | Wolfe et al. |
| 2012/0041294 | A1 | 2/2012 | Bai |
| 2012/0109262 | A1 | 5/2012 | Martens et al. |
| 2012/0279852 | A1 | 11/2012 | Zach |
| 2013/0030500 | A1 | 1/2013 | Toader et al. |
| 2013/0175733 | A1 | 7/2013 | De et al. |
| 2013/0190586 | A1 | 7/2013 | Akingba et al. |
| 2013/0274843 | A1 | 10/2013 | Barker et al. |
| 2014/0107728 | A1 | 4/2014 | Fried et al. |
| 2014/0309548 | A1 | 10/2014 | Merz et al. |
| 2014/0330354 | A1 | 11/2014 | Shelton et al. |
| 2014/0350634 | A1 | 11/2014 | Grill et al. |
| 2015/0065831 | A1 | 3/2015 | Popovic et al. |
| 2016/0128588 | A1 | 5/2016 | Melosh et al. |
| 2016/0302687 | A1 | 10/2016 | Lee et al. |

OTHER PUBLICATIONS

Bouton, C. et al., Restoring cortical control of functional movement in a human with quadriplegia. Nature, 2016; vol. 000, 13 pages.

Brenner, W. Use underfill encapsulants to enhance flip-chip assembly reliability. Electronic Design. Jul. 30, 2012; Retrieved Feb. 29, 2016 available at http://electronicdesign.com/boards/useunderfillencapsulantsenhanceflipchipassemblyreliability.

Hajjhassan et al. NeuroMEMS: Neural Probe Microtechnologies. Sensors 8(10):6704-6726 (Oct. 25, 2008). doi: https://doi.org/10.3390/s8106704.

Instruction for use (IFU) Blackrock research assemblies. Blackrock Microsystems, LLC. 2014. pp. 0-13.

International Search Report dated Jun. 19, 2017 for International Application No. PCT/US2017/026707.

Johnson, L.J. et al., A novel high electrode count spike recording array using an 81,920 pixel transimpedance amplifier-based imaging chip. Journal of Neuroscience methods. 205; 2012: 223-232.

Office Action dated Jun. 30, 2017 for U.S. Appl. No. 15/482,583.

Office Action dated Nov. 28, 2017 for U.S. Appl. No. 15/482,583.

PCT/US2018/025576 International Search Report and Written Opinion dated Jul. 30, 2018.

Scribner, D. et al., A retinal prosthesis technology based on CMOS microelectronics and microwire glass electrodes. IEEE transactions on biomedical circuits and systems, 1(1); Mar. 2007: p. 73-84.

U.S. Appl. No. 15/482,583 Notice of Allowance dated Mar. 6, 2019.

U.S. Appl. No. 15/482,583 Office Action dated Aug. 28, 2018.

U.S. Appl. No. 15/482,583 Notice of Allowance dated Apr. 23, 2019.

U.S. Appl. No. 15/482,583 Notice of Allowance dated Mar. 20, 2019.

* cited by examiner

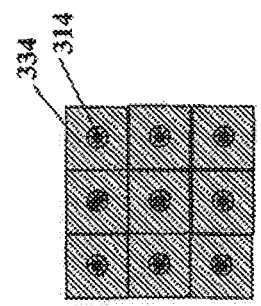
Figure 3B
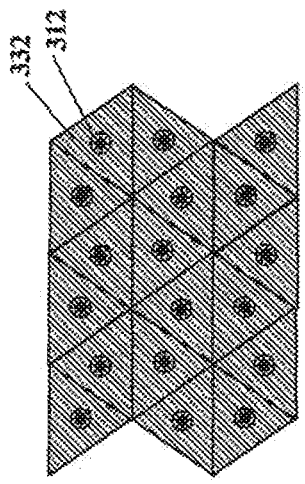
Figure 3C
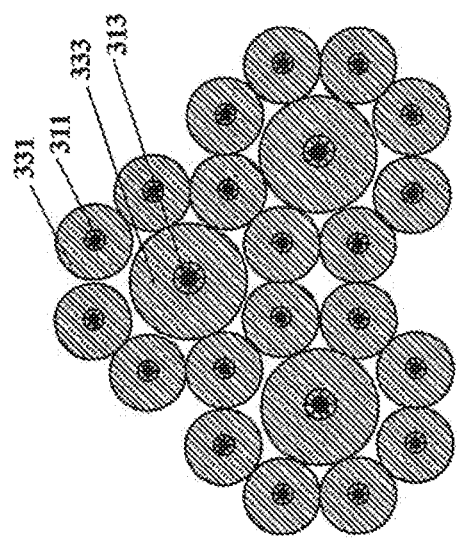
Figure 3A
Figure 3D

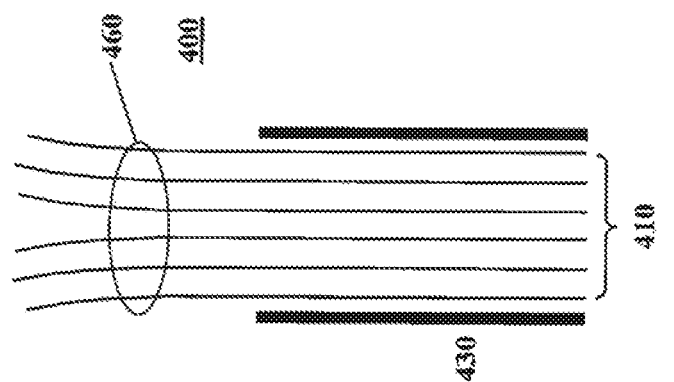

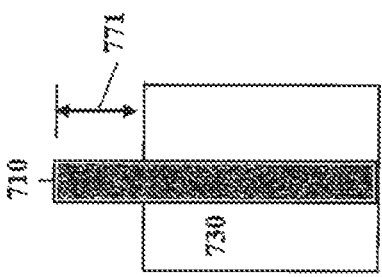
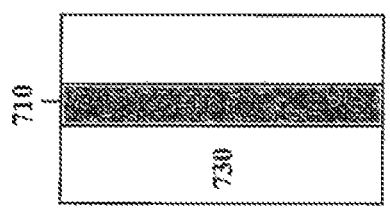
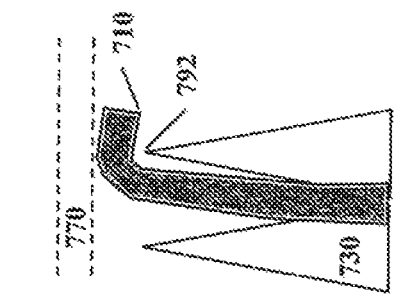
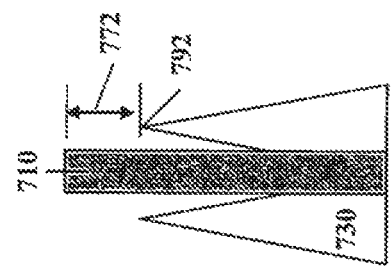
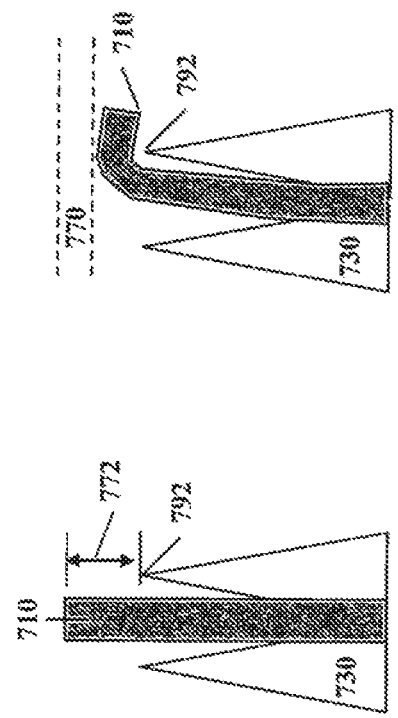
Figure 7A
Figure 7B
Figure 7C
Figure 7D
Figure 7E

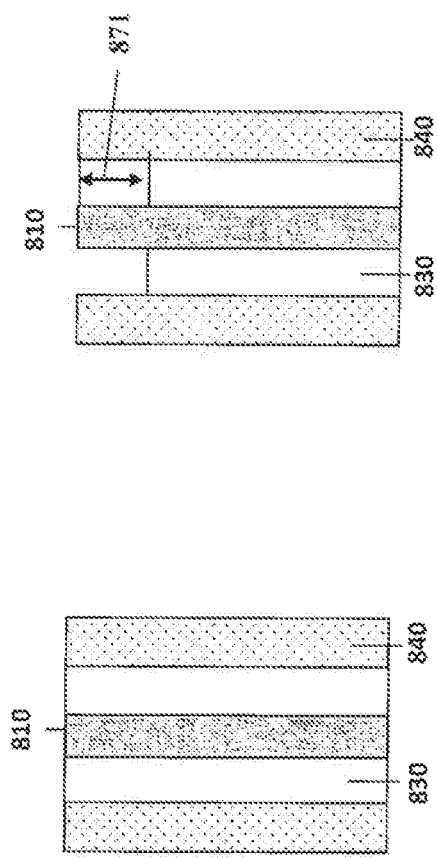
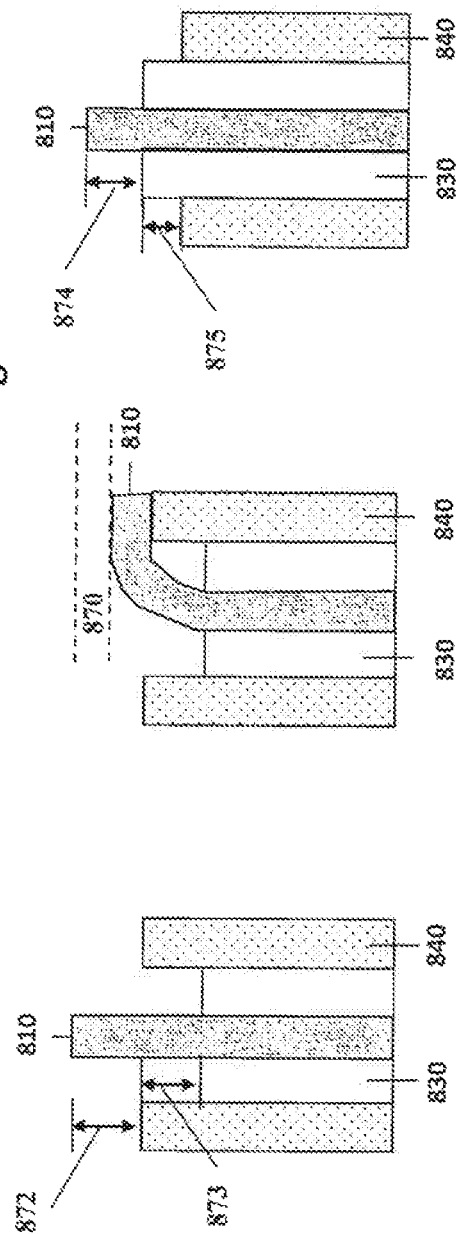
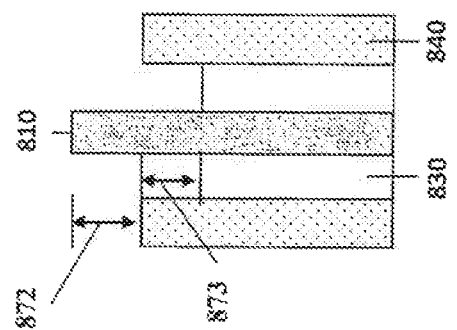

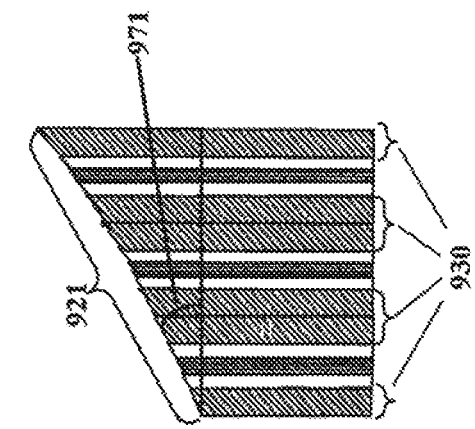
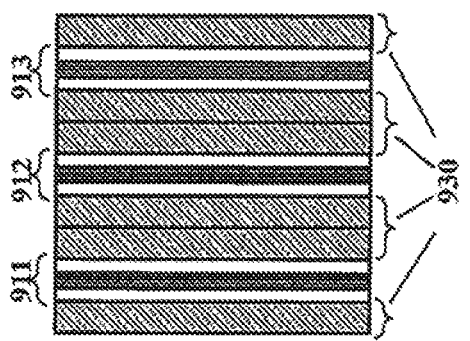
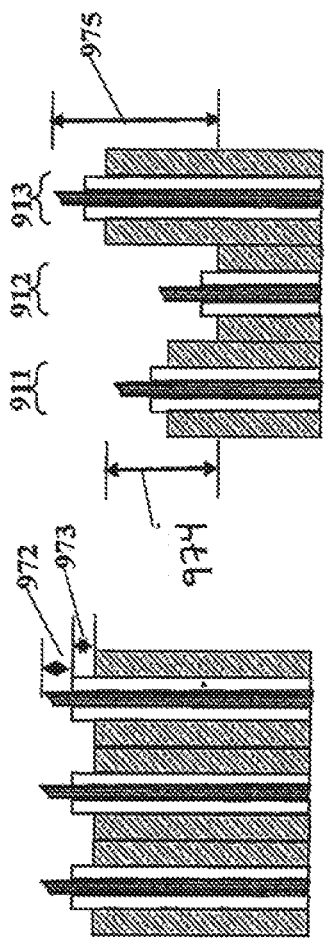
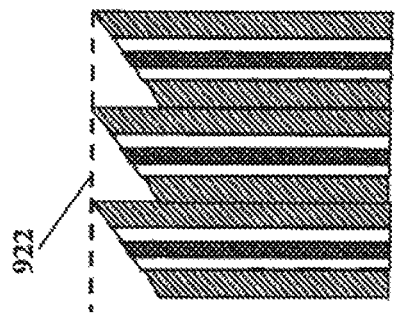

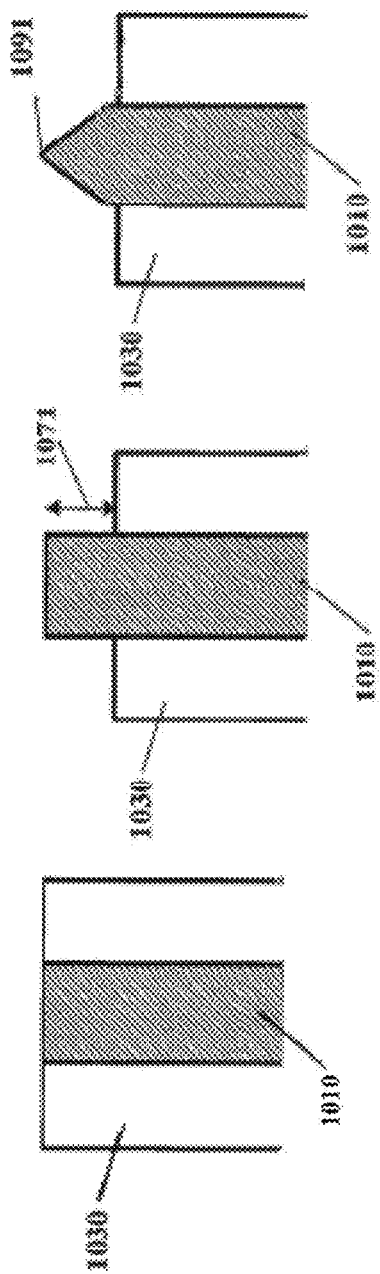

METHOD OF PRODUCING PATTERNED MICROWIRE BUNDLES

CROSS-REFERENCE

This application is a continuation application of International Application No. PCT/US18/25576, filed on Mar. 30, 2018, which application claims the benefit of U.S. Provisional Application No. 62/479,291, filed Mar. 30, 2017, which all applications are incorporated herein by reference in their entirety.

STATEMENT AS TO FEDERALLY SPONSORED RESEARCH

This work was supported by an SBIR grant from the National Institute of Health under Grant Number: 1 R43 MH110287-01.

BACKGROUND

High density neural recording probes can be used to gather electrical signals from the brain. Once recorded, these signals can be used to better understand the function of neural circuits, or the signals can be used to enable brain-control of computers and other prosthetic devices.

In addition to recording electrical signals, high density electrical probes can also be used to stimulate brain activity by passing current into the brain in defined spatiotemporal patterns. This activation may be used to study neural function in combination with recording and observation, or it may be used to reconstitute lost input to the brain as is found in sensory deficits such as blindness or deafness. Combined neural recording and stimulation may also be used to control ongoing neural dynamics, such as disrupting pathological patterns of activity associated with seizure or tremor.

In the design of such electrical probes for neural research, several parameters are important, for example, electrical recording or stimulation quality, biological safety (minimizing injury or trauma to the surrounding brain tissue), ease of manufacturing of the electrical probe, and the ability to integrate the electrical probe into an active electronic device. It would be therefore be desirable to present electrical probe designs and manufacturing techniques to achieve such goals.

SUMMARY

According to an aspect of the disclosure, a method for forming a bundle of microelectrodes is provided. The method may comprise coating a microwire comprising a first cladding layer with a second cladding layer to form a multiclad microwire; wrapping the multiclad microwire repeatedly around a spool; cutting the multiclad microwire on the spool to form a stack of cut multiclad microwires; and securing the stack of cut multiclad microwires together to form the bundle of microelectrodes.

In some embodiments, the method of forming a bundle of microelectrodes can include removing a portion of the first cladding layer at a first end of the stack of cut multiclad microwires to expose an electrical conductor at the first end of the stack. In some embodiments, the method of forming a bundle of microelectrodes can further include removing a portion of the first cladding layer at a first end of the stack of cut multiclad microwires to expose an electrical conductor at the first end of the stack; and removing a portion of the second cladding layer at the first end of the stack of cut multiclad microwires. In some embodiments, the method of forming a bundle of microelectrodes can include a second cladding layer which comprises a polymer. In some embodiments, the method of forming a bundle of microelectrodes can include a second cladding layer which is shaped to control an organization of the stack of cut multiclad microwires.

In some embodiments, the method of forming a bundle of microelectrodes can further include arranging the multiclad microwire into a desired pattern as the multiclad microwire is being wrapped around the spool. In some embodiments, the method of forming a bundle of microelectrodes can include a stack of cut multiclad microwires which is secured together by clamping the cut multiclad microwires in a heat shrink tubing. In some embodiments, the method of forming a bundle of microelectrodes can include a stack of cut multiclad microwires which is secured together by clamping the cut multiclad microwires within a rigid tube.

In some embodiments, the method of forming a bundle of microelectrodes can include a microwire which comprises a metal with a melting point exceeding 300 degrees Celsius. In some embodiments, the method of forming a bundle of microelectrodes can include a microwire comprising a first cladding layer which comprises glass. In some embodiments, the method of forming a bundle of microelectrodes can include a microwire comprising a first cladding layer which comprises ceramic.

In some embodiments, the method of forming a bundle of microelectrodes can further include polishing an end of one or more of the cut multiclad microwires at an angle that is not perpendicular to a longitudinal axis of said multiclad microwire(s). In some embodiments, the method of forming a bundle of microelectrodes can further include staggering one or more of the cut multiclad microwires relative to one another such that the stack of cut multiclad microwires comprises different lengths or extends to different depths. In some embodiments, the method of forming a bundle of microelectrodes can further include planarizing one or more end portions of the bundle of microelectrodes.

In some embodiments, the method of forming a bundle of microelectrodes can include a microwire which comprises a first cladding layer and a second cladding layer which have substantially different physical properties including melting point, softening point, and/or thermal expansion coefficient. In some embodiments, the method of forming a bundle of microelectrodes can include removing the portion of the first cladding layer which results in a conical pipette geometry due to differential etching between the electrical conductor and first cladding layer. In some embodiments, the method of forming a bundle of microelectrodes can include distal tips of the bundle of microelectrodes which are configured to lie within a defined manifold or volume in order to record from specific brain structures. In some embodiments, the method of forming a bundle of microelectrodes can include a distal tip of each of the cut multiclad microwires which is modified by depositing an electrode material onto a polished face of the cut multiclad microwire. In some embodiments, the method of forming a bundle of microelectrodes can include proximal tips of the bundle of microelectrodes which are modified by depositing a material which improves metal adhesion and solderability at a surface of the proximal tips.

In some embodiments, the method of forming a bundle of microelectrodes can include selective removal of the first cladding layer and an embedding material which allows the electrical conductor to be exposed. In some embodiments, the method of forming a bundle of microelectrodes can include exposed electrical conductors on proximal ends of the microwires which are used for bonding to readout electronics. In some embodiments, the method of forming a bundle of microelectrodes can include exposed electrical conductors on distal ends of the microwires which are used as large surface area electrodes for tissue penetration. In some embodiments, the method of forming a bundle of microelectrodes can include selective etching of the first cladding layer which results in a conical pipette geometry due to differential etching at an interface between the electrical conductor and the first cladding layer. In some embodiments, the method of forming a bundle of microelectrodes can include removal of a portion of the second cladding layer which exposes the first cladding layer as a primary contact surface. In some embodiments, the method of forming a bundle of microelectrodes can include removal of a portion of the first cladding layer which exposes the second cladding layer as a primary contact surface.

Another aspect of the disclosure is directed to a method for forming a bundle of microelectrodes. The method may comprise coating a set of microwires with a shaped coating material to create a set of coated microwires; arranging the set of coated microwires in a desired pattern, wherein the desired pattern comprises parallel coated microwires; and clamping the parallel coated microwires to form the bundle of microelectrodes. In some embodiments, the method for forming a bundle of microelectrodes can further include removing a portion of the shaped coating material at a first end of the parallel coated microwires to expose conductors of the parallel microwires.

In some embodiments, the method for forming a bundle for microelectrodes can include a microwire comprising a shaped coating material which comprises a polymer. In some embodiments, the method for forming a bundle for microelectrodes can include clamping the parallel coated microwires which comprises placing the set of coated microwires in a heat shrink tubing. In some embodiments, the method for forming a bundle for microelectrodes can include clamping the parallel coated microwires which comprises placing the set of coated microwires within a rigid tube. In some embodiments, the method for forming a bundle for microelectrodes can include an inner conductor in the microwires which comprises a metal with a melting point exceeding 300 degrees Celsius. In some embodiments, the method for forming a bundle for microelectrodes can include an insulator on the microwires which comprises glass. In some embodiments, the method for forming a bundle for microelectrodes can include an insulator on the microwires which comprises a ceramic.

In some embodiments, the method for forming a bundle for microelectrodes can include polishing an end of the coated microwires at an angle that is not perpendicular to a longitudinal axis of the microwires. In some embodiments, the method for forming a bundle for microelectrodes can further include staggering the coated microwires such that the coated microwires extend longitudinally to different depths. In some embodiments, the method for forming a bundle for microelectrodes can further include planarizing one or more end portions of the bundle of microelectrodes.

Another aspect of the present disclosure provides a microelectrode bundle for neural testing. The microelectrode bundle may comprise a set of microwires arranged substantially in parallel, each microwire comprising a conductive core and an insulative cladding; and an additional cladding layer added in-between the parallel microwires to control spacing and organization of the microwires in the microelectrode bundle. In some embodiments, the microelectrode bundle for neural testing may include a portion of the additional cladding layer and/or the insulative cladding which is selectively removed. In some embodiments, the microelectrode bundle for neural testing may include an additional cladding layer which is shaped to control the organization of the microwires.

In some embodiments, the microelectrode bundle for neural testing may include an additional cladding layer which comprises a polymer. In some embodiments, the microelectrode bundle for neural testing may include a set of microwires with an additional cladding layer which is clamped within a rigid tube. In some embodiments, the microelectrode bundle for neural testing may include a conductive core which comprises a metal with a melting point exceeding 300 degrees Celsius. In some embodiments, the microelectrode bundle for neural testing may include an insulative cladding which comprises glass. In some embodiments, the microelectrode bundle for neural testing may include an insulative cladding which comprises ceramic.

In some embodiments, the microelectrode bundle for neural testing may include parallel microwires which are staggered to extend longitudinally to different depths. In some embodiments, the microelectrode bundle for neural testing may include distal tips of the microwires which lie within a defined manifold or volume in order to record from specific brain structures.

In some embodiments, the microelectrode bundle for neural testing may include a distal tip of each microwire which is modified by deposition of an electrode material onto a polished face at said distal tip. In some embodiments, the microelectrode bundle for neural testing may include a proximal tip of each microwire which is modified by deposition of a material for aiding metal adhesion and solderability at a surface of said proximal trip. In some embodiments, the microelectrode bundle for neural testing may include removal of portions of the additional cladding layer and/or the insulative cladding which exposes a portion of the conductive core. In some embodiments, the microelectrode bundle for neural testing may include an exposed portion of the conductive core at a proximal end of the bundle which is used for bonding to readout electronics. In some embodiments, the microelectrode bundle for neural testing may include an exposed portion of the conductive core at a distal end of the bundle which is used as a high surface area electrode.

In some embodiments, the microelectrode bundle for neural testing may include selective etching of the insulative cladding which results in a conical pipette geometry due to differential etching at an interface between the conductive core and the insulative cladding. In some embodiments, the microelectrode bundle for neural testing may include removal of a portion of the insulative cladding which exposes the additional cladding layer as a primary contact surface. In some embodiments, the microelectrode bundle for neural testing may include removal of a portion of the additional cladding layer which exposes the insulative cladding as a primary contact surface.

Another aspect of the present disclosure provides a method for forming a bundle of microelectrodes. The method for forming a bundle of microelectrodes may comprise arranging a bundle of microwires in a desired pattern, wherein each of the microwires comprises a coating layer, and the desired pattern comprises parallel microwires; cutting the bundle of microwires to establish an end surface of the bundle of microwires; depositing a conductor material on the end surface of the bundle of microwires in contact with the coating layer; and removing a portion of the coating layer on the microwires near the end surface of the microwires such that a portion of the conductor material is no longer supported by the removed portion of the coating material and flakes off.

In some embodiments, the method for forming a bundle of microelectrodes may include depositing the conductor material which comprises electroplating the conductor material on the end surface of the bundle of microwires. In some embodiments, the method for forming a bundle of microelectrodes may include depositing the conductor material which comprises vapor deposition of the conductor material on the end surface of the bundle of microwires. In some embodiments, the method for forming a bundle of microelectrodes may include a coating layer which comprises a polymer.

In some embodiments, the method for forming a bundle of microelectrodes may further include polishing an end of the coated microwires at an angle that is not perpendicular to a longitudinal axis of the microwires. In some embodiments, the method for forming a bundle of microelectrodes may further include staggering the coated microwires such that the coated microwires extend longitudinally to different depths. In some embodiments, the method for forming a bundle of microelectrodes may further include planarizing the bundle of microelectrodes. In some embodiments, the method for forming a bundle of microelectrodes may include removal of portions of an inner cladding layer and the coating layer which exposes an inner conductor of each microwire. In some embodiments, the method for forming a bundle of microelectrodes may include exposed conductors at a proximal end of the bundle which are used for bonding to readout electronics. In some embodiments, the method for forming a bundle of microelectrodes may include exposed conductors at a distal end of the bundle which are used as high surface area electrodes. In some embodiments, the method for forming a bundle of microelectrodes may include selective etching of the inner cladding layer which results in a conical pipette geometry due to differential etching at an interface between the conductor and the inner cladding layer.

Another aspect of the disclosure provides a method for forming a bundle of microelectrodes. A method for forming a bundle of microelectrodes may comprise coating an insulator layer around a set of microwires with a shaped coating; arranging a bundle of microwires in a desired pattern by arranging the set of microwires with the shaped coating in parallel such that the shaped coating arranges the set of microwires into the desired pattern; and permanently locking the set of microwires in the parallel arrangement to hold the microwires in the desired pattern.

In some embodiments, a method for forming a bundle of microelectrodes may include a shaped coating which comprises a circular shape. In some embodiments, a method for forming a bundle of microelectrodes may include a shaped coating which comprises a square shape. In some embodiments, a method for forming a bundle of microelectrodes may include a shaped coating which comprises a triangular shape. In some embodiments, a method for forming a bundle of microelectrodes may include coating the insulator layer around the set of microwires with the shaped coating which comprises extruding the microwires through a coating applicator. In some embodiments, a method for forming a bundle of microelectrodes may include planarizing one or more end portions of the bundle of microelectrodes.

Another aspect of the present disclosure provides a method for forming a bundle of microelectrodes. A methods for forming a bundle of microelectrodes comprises arranging a bundle of microwires in a desired pattern by braiding a set of microwires such that the set of microwires is braided into a first braided set of microwires having the desired pattern; and permanently locking the first braided set of microwires in the braided arrangement to hold the desired pattern.

In some embodiments, a method for forming a bundle of microelectrodes may include braiding the set of microwires around a different sized wire. In some embodiments, a method for forming a bundle of microelectrodes may include braiding the first braided set of microwires around at least one other set of microwires to create a second desired pattern. In some embodiments, a method for forming a bundle of microelectrodes may include planarizing one or more end portions of the bundle of microelectrodes.

Another aspect of the present disclosure provides a method for forming a bundle of microelectrodes. A method for forming a bundle of microelectrodes may comprise arranging a bundle of microwires in a desired pattern, wherein the desired pattern comprises parallel microwires; adding a sacrificial material between the parallel microwires to hold the microwires in the desired pattern; and removing a portion of the sacrificial material at a first end of the parallel microwires to expose inner conductors of the microwires.

In some embodiments, a method for forming a bundle of microelectrodes may include a sacrificial material which comprises wax. In some embodiments, a method for forming a bundle of microelectrodes may include a sacrificial material which comprises an epoxy. In some embodiments, a method for forming a bundle of microelectrodes may include placing the bundle of microwires in a heat shrink tube. In some embodiments, a method for forming a bundle of microelectrodes may include placing the bundle of microwires in a rigid tube.

Another aspect of the present disclosure provides a method for forming a bundle of microelectrodes. A method for forming a bundle of microelectrodes may comprise coating an insulator layer around a set of microwires with a shaped coating; arranging a bundle of microwires in a desired pattern by arranging the set of microwires with the shaped coating in parallel such that the shaped coating arranges the set of microwires into the desired pattern; and permanently locking the set of microwires in the parallel arrangement to hold the microwires in the desired pattern.

In some embodiments, a method for forming a bundle of microelectrodes may include a shaped coating comprises a circular shape. In some embodiments, a method for forming a bundle of microelectrodes may include a shaped coating which comprises a square shape. In some embodiments, a method for forming a bundle of microelectrodes may include a shaped coating which comprises a triangular shape. In some embodiments, a method for forming a bundle of microelectrodes may include coating the insulator layer around the set of microwires with the shaped coating which comprises extruding the microwires through a coating applicator.

Another aspect of the present disclosure provides method for forming a bundle of microelectrodes. A method for forming a bundle of microelectrodes may comprise arranging a bundle of microwires in a desired pattern by braiding a set of microwires such that the set of microwires is braided into a first braided set of microwires having the desired pattern; and permanently locking the first braided set of microwires in the braided arrangement to hold the microwires in the desired pattern. In some embodiments, the method for forming a bundle of microelectrodes may include a set of microwires which is braided around a different sized wire. In some embodiments, the method for forming a bundle of microelectrodes may include a first braided set of microwires which is braided around at least one other set of microwires to create a second desired pattern.

In another aspect the present disclosure provides a bundle of microelectrodes. A bundle of microelectrodes may comprise a plurality of microwires each comprising a conductive core and an insulative cladding, wherein a spacing and arrangement of the microwires within the bundle is dictated by a thickness and geometry of one or more additional cladding layers that can be selectively removed, wherein the microwires are bound together by a polymer embedding matrix, and wherein distal and proximal ends of the bundle are independently patterned by selective removal of the insulative cladding, the one or more cladding layers, and/or the embedding matrix.

In some embodiments, the bundle of microelectrodes may include a conductive core which comprises a metal with a melting point exceeding 300 degrees Celsius. In some embodiments, the bundle of microelectrodes may include an insulative cladding which comprises glass or ceramic. In some embodiments, the bundle of microelectrodes may include additional cladding layers at least one of which comprises a polymer. In some embodiments, the bundle of microelectrodes may include distal ends of the microwires within the bundle which are polished at an angle that is not perpendicular to a longitudinal axis of the microwires. In some embodiments, the bundle of microelectrodes may include microwires extend at staggered lengths such that distal tips of the microwires record at different depths in a brain. In some embodiments, the bundle of microelectrodes may include distal tips of the microwires which lie within a defined manifold or volume in order to record from specific brain structures.

In some embodiments, the bundle of microelectrodes may include a distal tip of each microwire which is modified by deposition of an electrode material onto a polished face of said distal tip. In some embodiments, the bundle of microelectrodes may include a proximal tip of each microwire which is modified by deposition of a material for aiding metal adhesion and solderability at a surface of said proximal tip. In some embodiments, the bundle of microelectrodes may include removal of portions of the insulative cladding, the cladding layers, and/or the embedding matrix which exposes the conductive core, wherein the exposed conductive core at a proximal end of the bundle is used for bonding to readout electronics, and the exposed conductive core at a distal end of the bundle is used as a high surface area electrode.

In some embodiments, the bundle of microelectrodes may include etching of the insulative cladding which results in a conical pipette geometry due to differential etching at an interface between the conductive core and the insulative cladding. In some embodiments, the bundle of microelectrodes may include at least two of the following: (1) conductive core; (2) insulative cladding; (3) the one or more additional cladding layers; or the (4) embedding matrix, which have substantially different physical properties including melting point, softening point, and/or thermal expansion coefficient such that the bundle is not formable using only a drawing process. In some embodiments, the bundle of microelectrodes may include removal of the insulative cladding which exposes the one or more additional cladding layers as a primary contact surface. In some embodiments, the bundle of microelectrodes may include removal of the one or more additional cladding layers which exposes the insulative cladding as a primary contact surface.

Another aspect of the present disclosure provides a method of forming a bundle of microelectrodes. A method of forming a bundle of microelectrodes may comprise re-spooling a length of insulated microwire; coating the insulated microwire with additional cladding layers either as part of the re-spooling process or directly following the re-spooling process; cutting the coated microwire to form a stack of cut microwires after the microwire has been coated with the additional cladding layers, wherein multiple stacks of a same or different wire types can be combined to form larger stacks; and embedding the stack of cut microwires in a removable material for planarization of a distal end of the bundle.

In some embodiments, a method of forming a bundle of microelectrodes may further include dissolution of the removable material and re-stacking the microwires such that distal tips of the microwires are located with a defined manifold or volume; re-embedding the stack of microwires or a portion thereof including a proximal end of the bundle in a polymer resin; and planarizing the proximal end of the bundle by removing excess polymer resin. In some embodiments, a method of forming a bundle of microelectrodes may include one or more of additional cladding layers which is applied through an in-line coating process comprising coating of UV- or heat-curable polymers. In some embodiments, a method of forming a bundle of microelectrodes may include one or more of the additional cladding layers which is applied through an extrusion process.

Another aspect of the present disclosure provides, a method of forming a bundle of microelectrodes. A method of forming a bundle of microelectrodes may comprise providing a bundle of microwires each comprising a conductive core and an insulative coating; removing a portion of the insulative coating of each microwire to expose an end portion of the conductive core of the microwire; and performing an electrochemical modification of the end portions of the conductive cores to form a plurality of sharp conductive tips protruding from the insulative coatings of the microwires.

Another aspect of the present disclosure provides, a method of forming a bundle of microelectrodes. A method of forming a bundle of microelectrodes may comprise providing a bundle of microwires each comprising a conductive core and an insulative coating; etching a portion of the conductive core of each microwire such that an end portion of the conductive core is recessed within the insulative coating of the microwire; and performing an electrochemical modification of the end portions of the conductive cores to form a plurality of sharp conductive tips recessed within the insulative coatings of the microwires.

In some embodiments a method of forming a bundle of microelectrodes may include electrochemical modification which comprises a subtractive process or an additive process. In some embodiments, a method of forming a bundle of microelectrodes may include electrochemical modification which is carried out in an electrically conductive bath. In some embodiments, a method of forming a bundle of microelectrodes may include a bundle of microelectrodes which comprises the plurality of sharp conductive tips at a distal end and/or proximal end of the bundle. In some embodiments, a method of forming a bundle of microelectrodes may include a plurality of sharp conductive tips each of which comprises an apex. In some embodiments, a method of forming a bundle of microelectrodes may further include removing a portion of the insulative coating of each microwire such that the plurality of sharp conductive tips protrude from the insulative coatings of the microwires.

Another aspect of the present disclosure provides a method of forming a bundle of microelectrodes. A method of forming a bundle of microelectrodes may comprise providing a bundle of microwires each comprising a conductive core and an insulative coating; electrodepositing a material on an exposed top portion of each microwire; and removing a portion of the insulative coating of each microwire to expose a side portion of the conductive core of the microwire, wherein the electrodeposited material remains bonded to the exposed top portion of each microwire after the portion of the insulative coating of each microwire has been removed.

Another aspect of the present disclosure provides a method of forming a bundle of microelectrodes. A method of forming a bundle of microelectrodes may comprise providing a bundle of microwires each comprising a conductive core and an insulative coating, wherein the conductive core comprises an exposed top portion; removing a portion of the insulative coating of each microwire to further expose a side portion of the conductive core; and electrodepositing a material on the exposed top and side portions of each microwire. In some embodiments, a method of forming a bundle of microelectrodes may further include removing the insulative coating of each microwire to expose the remaining side portion of the conductive core of the microwire, wherein the electrodeposited material remains bonded to the exposed top and side portions of each microwire after the insulative coating of each microwire has been removed. In some embodiments, a method of forming a bundle of microelectrodes may include a material which aids in bonding the conductive core to a readout integrated circuit.

Another aspect of the present disclosure provides a method of forming a bundle of microelectrodes. A method of forming a bundle of microelectrodes may comprise providing a bundle of microwires each comprising a conductive core and an insulative coating; etching a portion of the conductive core of each microwire such that an end portion of the conductive core is recessed within the insulative coating of the microwire; electrodepositing a material over the microwires onto the recessed conductive core; applying a planarization step to remove excess electrodeposited material; removing a portion of the insulative coating of each microwire to expose the electrodeposited material on top of the conductive core; and performing an electrochemical modification of the electrodeposited material to form a plurality of sharp conductive tips protruding from the insulative coatings of the microwires.

Another aspect of the present disclosure provides a method of forming a bundle of microelectrodes. A method of forming a bundle of microelectrodes may comprise providing a bundle of microwires each comprising a conductive core and an insulative coating; etching a portion of the conductive core of each microwire such that an end portion of the conductive core is recessed within the insulative coating of the microwire; electrodepositing a material over the microwires onto the recessed conductive core; applying a planarization step to remove excess electrodeposited material; and performing an electrochemical modification of the electrodeposited material to form a plurality of sharp conductive tips recessed within the insulative coatings of the microwires. In some embodiments a method of forming a bundle of microelectrodes may further include removing a portion of the insulative coating of each microwire such that the plurality of sharp conductive tips protrude from the insulative coatings of the microwires.

Another aspect of the present disclosure provides an electrochemical modification apparatus. An electrochemical modification apparatus may comprise an electrochemical bath comprising a counter electrode connected to a voltage or current source; and a bundle of electrodes configured to be electrochemically modified by the electrochemical bath and by controlling the voltage or current source to form a plurality of sharpened tips.

In some embodiments the electrochemical modification apparatus may include a plurality of proximal ends of the bundle of electrodes that do not undergo electrochemical modification which are shorted together. In some embodiments the electrochemical modification apparatus may include a bundle of electrodes which is electrically coupled to a planar circuit comprising a pixel array, wherein the pixel array comprises an array of switches that are configured to control passing of current or application of voltage from the current/voltage source. In some embodiments the electrochemical modification apparatus may include electrochemical modification of each electrode in the bundle of electrodes is performed sequentially or in parallel. In some embodiments the electrochemical modification apparatus may include a pixel array wherein each pixel of the pixel array includes a current measurement circuit.

In some embodiments the electrochemical modification apparatus may include a plurality of distal ends of the bundle of electrodes which undergo electrochemical modification. In some embodiments the electrochemical modification apparatus may include shorted ends of the bundle of electrodes which are coupled to a single voltage/current source with an optional current readout. In some embodiments the electrochemical modification apparatus may include shorted ends of the bundle of electrodes which are not coupled to a pixel array. In some embodiments the electrochemical modification apparatus may include a plurality of sharpened tips each of which has a radius of less than about 1 um. In some embodiments the electrochemical modification apparatus may include a plurality of sharpened tips each of which has a radius of less than about 50 nm.

Optionally, in any aspect of the present disclosure, the bundle comprises at least 100 microelectrodes. Optionally, in any aspect of the present disclosure, the bundle comprises at least 1000 microelectrodes. Optionally, in any aspect of the present disclosure, the bundle comprises at least 10000 microelectrodes. Optionally, in any aspect of the present disclosure, the bundle comprises at least 100000 microelectrodes. Optionally, in any aspect of the present disclosure, the bundle may comprise at least 1000000 microelectrodes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the various principles are utilized, and the accompanying drawings of which:

FIG. 3A illustrates an end view of a microwire bundle with an added round coating to create a hexagonal close packed structure, in accordance with some embodiments.

FIG. 3B illustrates an end view of a microwire bundle with an added triangle shaped coating to create an offset pattern structure, in accordance with some embodiments.

FIG. 3C illustrates an end view of a microwire bundle with an added square shaped coating to create a Cartesian pattern structure, in accordance with some embodiments.

FIG. 3D illustrates an end view of a microwire bundle with an added larger wire to create a different organization, in accordance with some embodiments.

FIG. 4A illustrates a cross-section view of a set of microwires held within a rigid tube, in accordance with some embodiments.

FIG. 7A illustrates the end of a microwire having a central conductor core surrounded by a cladding insulator, in accordance with some embodiments.

FIG. 7B illustrates uniform removal of cladding material from the microwire end of FIG. 7A, in accordance with some embodiments.

FIG. 7C illustrates non-uniform removal of cladding material from the microwire end of FIG. 7A forming a pipette structure, in accordance with some embodiments.

FIG. 7D illustrates non-uniform removal of cladding material from the microwire end of FIG. 7A forming a pipette structure with an extended conductor, in accordance with some embodiments.

FIG. 7E illustrates the microwire end of FIG. 7D with the conductor bent from pressing against a contact, in accordance with some embodiments.

FIG. 8A illustrates a microwire with a multiclad insulator in accordance with some embodiments.

FIG. 8B illustrates removal of an inner cladding layer from the end of the multiclad microwire of FIG. 8A, in accordance with some embodiments.

FIG. 8C illustrates a limited removal of parts of both cladding layer from the multiclad microwire of FIG. 8A, in accordance with some embodiments.

FIG. 8D illustrates the multiclad microwire of FIG. 8C after the metal core has been pressed against a contact, in accordance with some embodiments.

FIG. 8E illustrates the multiclad microwire of FIG. 8A after a small portion of the inner cladding and a larger portion of the outer cladding have been removed, in accordance with some embodiments.

FIG. 9A illustrates a bundle of microwires held together with sacrificial coating material in accordance with some embodiments.

FIG. 9B illustrates the microwire bundle of FIG. 9A cut at an angle to create an edge, in accordance with some embodiments.

FIG. 9C illustrates the microwire bundle of FIG. 9B after rearranging the wire segments to be of equal length, in accordance with some embodiments.

FIG. 9D illustrates the microwire bundle of FIG. 9C after the cladding and coating material have been removed from the microwires, in accordance with some embodiments.

FIG. 9E illustrates the microwire bundle of FIG. 9B after the cladding and coating material have been removed from the microwires, in accordance with some other embodiments.

FIG. 10A illustrates the end of a microwire which may be electropolished or electrosharpened, in accordance with some embodiments.

FIG. 10B illustrates the end of the microwire of FIG. 10A after the coating has been etched, in accordance with some embodiments.

FIG. 10C illustrates the end of the microwire of FIG. 10B after the wire has been sharpened, in accordance with some embodiments.

DETAILED DESCRIPTION

Figure 1A:
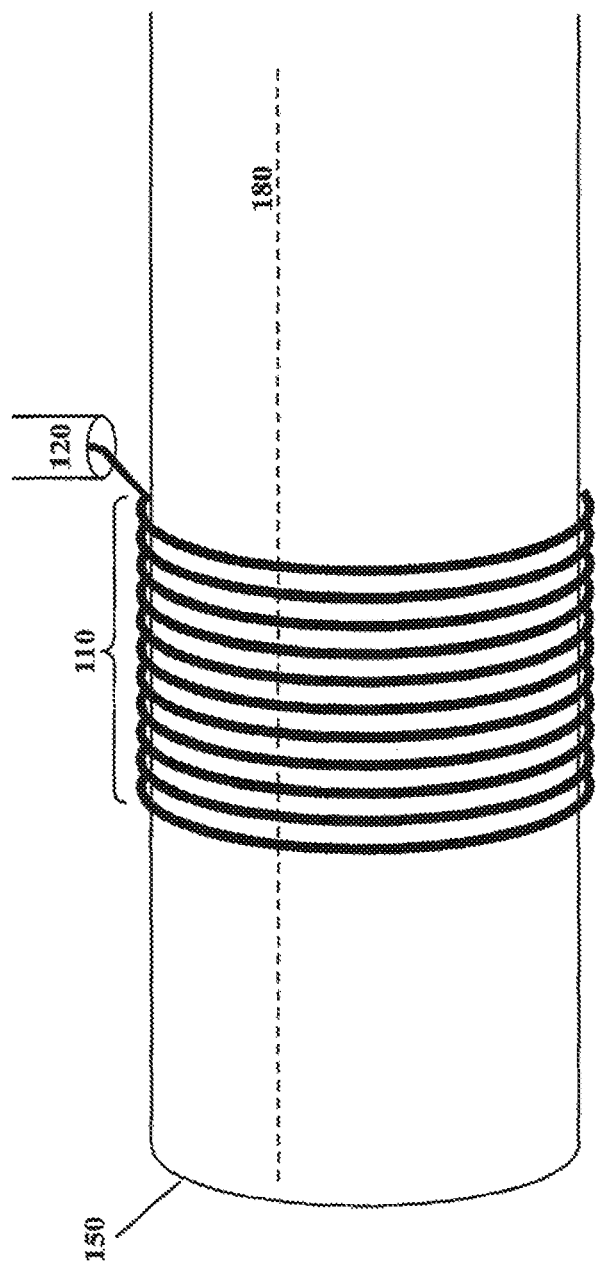
FIG. 1A illustrates bundling of microwires around a cylinder in accordance with some embodiments.

1. Microelectrode Background:

To obtain as much electrical activity information as possible, a bundle of hundreds or thousands of microelectrodes may be introduced into the brain or other electrically active soft tissue. However, a doctor or medical researcher may generally wish to minimize disruption of soft tissue in a subject when the bundle of microelectrodes is inserted into the soft tissue. It would therefore be desirable to implement systems and methods for creating medical microelectrodes that obtain as much electrical activity information as possible while minimizing disruption to the subject's soft tissue. To avoid significant tissue disruption, it is often desirable to reduce a size of individual microwires (e.g., <50 micrometers) and to control the spacing between the microwires/microelectrodes. In some instances, the terms "microwires" and "microelectrodes" may be used interchangeably as described herein. Examples of microwires, microelectrodes, bundles of microwires or microelectrodes, and methods for fabricating the aforementioned are described in U.S. patent application Ser. No. 15/482,583 (published as US 2017/0290521) entitled "Neural-Interface Probe and Methods of Packaging the Same" which is incorporated herein by reference.

In addition to controlling the general diameter and spacing of microwires within a bundle, it may also be desirable to control the surface properties of the microwire bundle. Namely, the brain-facing end of the bundle may comprise a spaced array of wires of a certain length or different lengths. The brain-facing end of the bundle may correspond to a distal end portion of the microwire bundle that is configured to be inserted into brain tissue. Shaping/forming this brain-facing surface is one form of patterning. Another form of patterning is the treatment of the brain-facing end of each individual microwire that forms the microelectrode. Finally, it may be desirable to treat the electronic device-facing end of the microwire bundle to increase fidelity of electrical and mechanical integration into the active electronic device. The device-facing end of the microwire bundle may correspond to a proximal end portion of the microwire bundle that is configured to be electrically coupled to a device chip. The device chip can include, for example a readout integrated circuit.

Creating microelectrode bundles of a particular geometry may be difficult due to the small scale and high precision which may be required. This is made even more challenging because the bundle may be patterned on both the brain-facing (distal or microelectrode) and the electronic device-facing (proximal or readout) end surfaces, that may not be compatible with traditional microfabrication techniques (i.e. lithography). It is therefore desirable to implement systems and methods for efficiently manufacturing effective microelectrode bundles. In this manner, reliable and highly effectively microelectrode bundles can be used to advance the state of science and medicine.

2. Microwire Bundle Fabrication Background:

In order to achieve high density and parallel electrical neural recordings, a plurality of highly parallelized microwires may be combined into a bundle with microelectrode ends that are capable of being inserted into neural tissue. These microwire bundles may be constructed in a variety of ways. One method of construction is to combine large numbers of glass-insulated metal-cored microwire segments together such that the group of microwire segments can be used as microelectrodes. The insulator material is also referred to as cladding, and may also comprise other ceramic materials or polymers. In some embodiments, the metal-core conductor is a metal with a melting point exceeding 300° C. such that high temperatures can be used to modify the insulator material without affecting the metal core.

These microwire segments may be bundled together in a parallel fashion with the proximal end connected to an electrical readout circuit and the distal/microelectrode end inserted into neural tissue to facilitate electrical recording.

The controlled organization and spacing of the microwires may help facilitate connection of the microelectrode bundles to the readout integrated circuit. The preparation of the microelectrode bundles may also be compatible with methods for subsequent preparation of the microelectrode bundle ends for further processing, such as chemical processing, mechanical processing, and other such methods. To accomplish these goals, one or more parameters may be carefully controlled during the manufacturing process. Examples of such parameters may include: the configuration (s) in which the microwire segments in the bundle are arranged, control of the microwire spacing and organization, the shape(s) of the resulting microwire bundles, and preparation of the surfaces on the two ends of the microwire bundles for different functionality.

The construction of microwire bundles can comprise at least some of the following steps in various combinations: (1) assembly of microwires into a microwire bundle arrangement, (2) embedding of the microwire bundle with a filler material to hold the bundle arrangement, (3) attaching the microwire bundle to a rigid connector for structural integrity, (4) polishing the end surfaces of the microwire bundle, and/or (5) modifying the microwire bundle surface into a desired shape.

3. Microelectrode Spacing and Organization:

The spacing and organization of microwires in a bundle can be important for at least the following reasons: 1) the yield of microwire-readout circuit electrical connectivity can be dependent on the spacing of the wires at the proximal/readout end of the microwire bundle relative to the contact pads in the readout array, and 2) the biological impact of the microelectrode/distal end of the microwires on the neural tissue can be dependent on the spacing and arrangement of the microwires at the microelectrode/distal end of the microwire bundle.

A method of bundling a microwire (e.g. 110) around a cylinder (e.g. 150) may include laying the microwire in a random configuration by wounding it around the cylinder. In some embodiments, the cylinder may be a spool, or may comprise a spool. The windings of microwire may be cut along an imaginary line (e.g. 180) and collected into short linear chains of cut microwires arranged in a random conformation. This random configuration method has the advantage of being simple and straightforward, but may have the disadvantage of resulting in random packing of microwires in a microwire bundle.

Figure 1B:
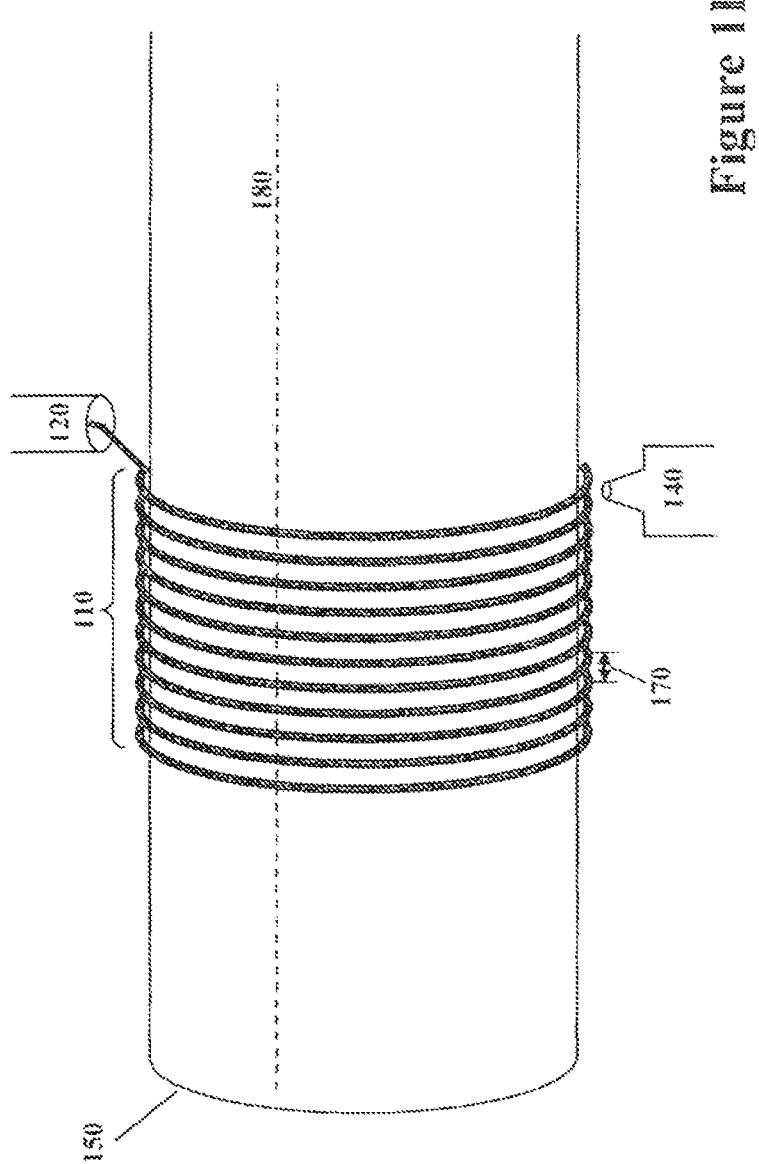
FIG. 1B illustrates the bundling of microwires around the cylinder of FIG. 1A and using adhesive to secure the microwires in place in accordance with some embodiments.

To improve packing of the cut microwires, an alternative method is to use a computer-controlled physical guide 120 to control how the microwire 110 is spaced and wound around the cylinder 150, before the windings of microwire are cut along the imaginary line 180 and subsequently bundled together, for example as shown in FIG. 1A. This controlled manner of bundling allows the cut microwires to be placed in a more organized configuration when the cut microwires are collected as a single microwire bundle. The physical guide 120 can be configured to lay the microwire around the cylinder such that adjacent windings of microwire are spaced apart by a distance 170, for example as shown in FIG. 1B. In some embodiments, the distance 170 may be less than 50 microns. Alternatively, the windings of microwire may be spaced apart by 1 micron, 2 microns, 5 microns, 10 microns, 20 microns, 50 microns, 100 microns, 200 microns, 500 microns, or any length within a range defined by any two of the preceding values.

To further control the creation of a microwire bundle, an adhesive may be applied during controlled bundling of microwires, for example as illustrated in FIG. 1B. An adhesive applicator 140 may be used to apply an adhesive (not shown) to secure the windings of microwire in place, and to maintain the organization of the windings of microwire as provided by the physical guide 120. The subsequent bundling of cut microwires with an adhesive technique allow the cut microwires to remain in an organized configuration, while the windings of microwire are being cut along the imaginary line 180 and collected as a single microwire bundle.

The guided microwire placement techniques illustrated in FIGS. 1A and 1B can be further modified by integrating heterogeneous wires together into a microwire bundle to achieve a greater variety in microwire patterns. For example, a plurality of different wire sizes can be used to increase the number of types of microwire pattern arrangements that can be created. Furthermore, the integration of heterogeneous wires can be used to achieve greater functionality. For example, wires of different diameters and/or of different materials can be bundled together having different microelectrodes, solution interface properties, or for providing different electrical functions (e.g., use as a reference or counter electrode). Different types of microwires in a single bundle can be used to penetrate different areas of tissue with different densities or properties tuned for different areas. Furthermore, different electrical and/or mechanical connections can be made with different microwire bundles on the distal/readout end with heterogeneous microwire bundles.

Figure 1C:
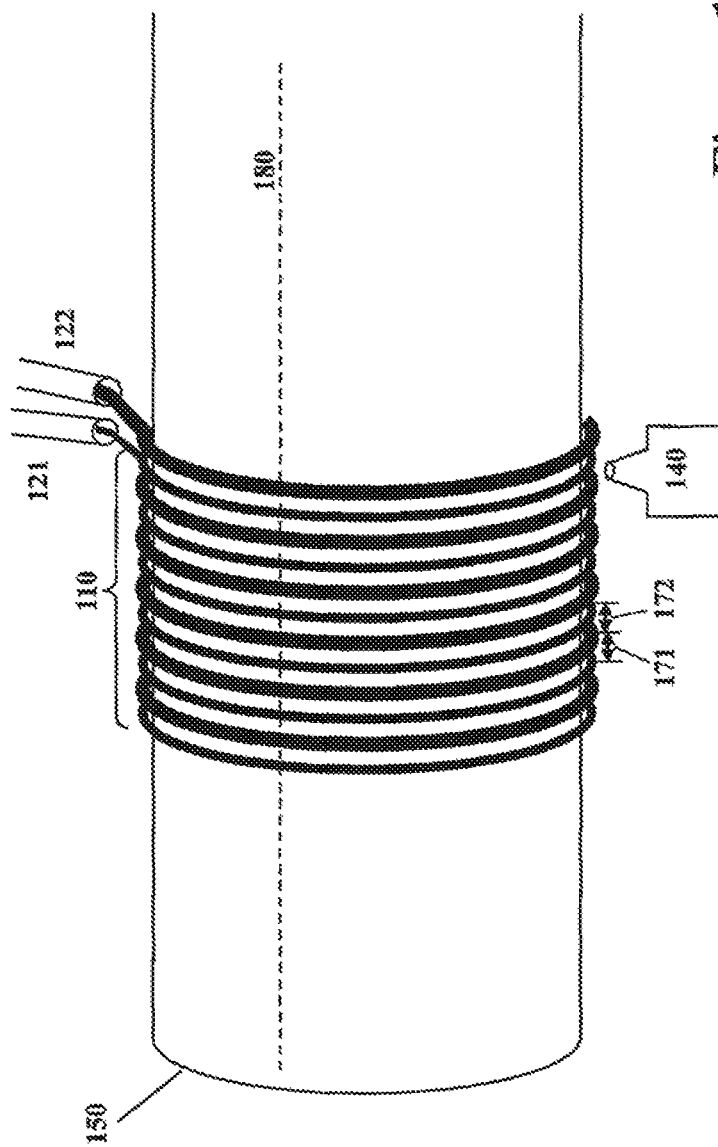
FIG. 1C illustrates the bundling of microwires of two different sizes around a cylinder in accordance with some embodiments.

FIG. 1C illustrates a system where two computer-controlled physical guides 121 and 122 may be used to guide two different sized microwires onto the cylinder 150 for creating microwire bundles. The physical guide 121 can be configured to wind a first microwire around the cylinder 150, and the second physical guide 122 can be configured to wind a second microwire around the cylinder 150. The first and second microwires may comprise a same material, or comprise different materials. The first and second microwires may be of different sizes. The different sizes of the microwires permit different microwire spacings and/or organizations. For example, the first and second microwires may be wound around the cylinder 150 having different spacings, for example comprise spacings 171 and 172 as shown in FIG. 1C. In some embodiments, spacing 172 may be larger than spacing 171. Alternatively, spacing 172 may be smaller than spacing 171. In some other cases, the spacings 171 and 172 may be substantially equal. In some cases, the spacings 171 and 172 may comprise distances that are similar to spacing 170 shown in FIG. 1B. The first and second microwires may or may not have the same sized conductor cores. It should be appreciated that the arrangement of FIG. 1C is illustrative of one embodiment, and that additional embodiments may include the use of three, four, or more different sized microwires. Any number of microwires, type, material, size, shape, and/or spacing of the microwires may be contemplated.

Other methods of controlling wire organization and spacing can include braiding of two or more microwires. The braided microwires may either be sacrificially coated, or alternatively braided with an additional coating to help control spacing and organization. To construct large bundles of microwire with intricate spacing patterns, braided microwires may be iteratively assembled as braids of microwires. Using such hierarchical braiding can enable a precise organizational control of the microwire bundle. Microwire braidings may also be conducted using a core material of a controlled or defined shape in order to improve organizational yield.

Other methods may also be used to control spacing and organization of the microwires that are used to create a microwire bundle. For example, another method of controlling spacing is by coating the outside of the microwires with a material to increase the size of the microwires. This additional coating material may result in spaced bundles due to the separation defined by the added material. The additional coating material may then be selectively removed once the bundle is assembled, resulting in microwires with a defined spacing therebetween, and voids in places where the coating material has been removed.

The coating material added to microwires may comprise different types of materials. One or more of the materials can be directly coated onto microwires in an in-line polymerization, solvent evaporation, or extrusion process. Alternatively, one or more of the materials may be deposited onto microwires using methods such as chemical or physical vapor deposition, in either an in-line or a batch process. In some embodiments, a paralyene coating may be used.

Coatings may be applied to microwire in an inline manner, using for example some methods of applying coatings to optical fibers that are known to those skilled in art. Such coatings may include crosslinkable polymers that are cured using heat, ultraviolet (UV), or solvent cast.

The microwire coating may comprise a single layer or multiple layers. Using multiple coatings can allow distal/microelectrode and proximal/readout ends to be etched selectively, and can enable the outer diameter of a glass insulating layer to be independently configured with respect to the spacings at the distal and proximal ends. For example, two coatings with different chemical properties may be used. Following embedding of the microwire bundle at the proximal/readout end, the outer sacrificial layer can be removed and re-embedded so that the spacing where the bundle meets the CMOS chip center is dictated by the inner spacing layer. Subsequently, at the distal/microelectrode end of the bundle, the glass-metal wires can be exposed by oxygen plasma treatment of both sacrificial layers to create a microwire array with spacing dictated by the outer diameter of the outermost coating.

A plurality of coatings (e.g. two coatings) with different chemical properties can be used to collect the wires into a condensed format, so as to utilize limited chip area more effectively. A plurality of coatings (e.g. two coatings) with different chemical properties can also be used to create an inner sacrificial layer, which may have a fixed spacing that is greater than the glass insulator diameter but less than the outer polymer coating diameter.

Using various multi-coating techniques, each coating layer may be deposited in a sequential process, for example by subjecting a microwire through successive in-line processes. Each layer of coating material may comprise different properties, including orthogonal removability (such as by different solvents), variable biocompatibility, and may be formed having different thicknesses and/or shapes. These coatings may be used for different functionalities, such as a thermoplastic coating layer over a thermoset polymer layer, or vice versa.

The coating material added to the microwires may be made of a material that can be removed in controlled manner, for example at the two ends of the microwires in order to better access the microwires and their cores. Thus, the coating material may be referred to herein interchangeably as a sacrificial material.

Figure 2B:
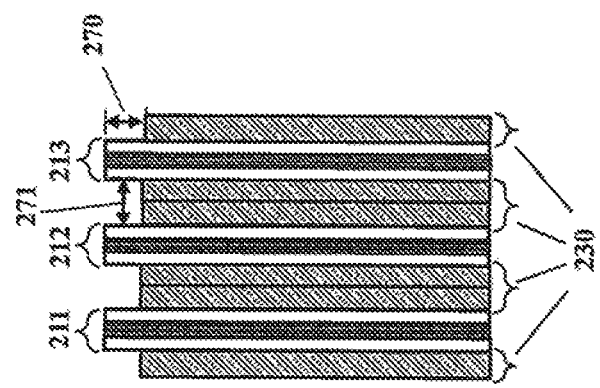
FIG. 2B illustrates the cross section of FIG. 2A whereby sacrificial coating material has been removed from an end portion of the bundle of microwires, in accordance with some embodiments.
Figure 2A:
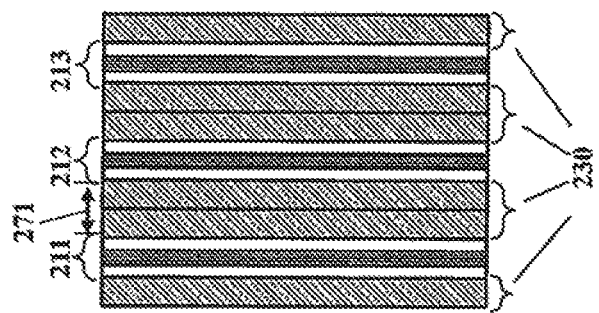
FIG. 2A illustrates a cross section of a bundle of three microwires comprising a sacrificial coating material, in accordance with some embodiments.

FIG. 2A illustrates a cross section of a bundle of three microwires 211, 212, and 213 that have added sacrificial coating material 230 to provide additional spacing between microwires 211, 212, and 213. Each of the microwires microwires 211, 212, and 213 may comprise an inner metal core and an outer insulating layer. In the illustrated embodiment, three microwires are shown. Any number of microwires may be contemplated. For example, bundles of microwires may comprise 2, 5, 10, 20, 50, 100, 200, 500, 1000, 2000, 5000, 10000, 20000, 50000, 10000, 100000, 1000000 or any number of microwires within a range defined by any two of the preceding values. In some embodiments, the spacing 271 between microwires may be between 30 microns and 50 microns. In other embodiments, the spacing 271 may be 1 microns, 2 microns, 5 microns, 10 microns, 20 microns, 50 microns, 100 microns, 200 microns, 500 microns, or any distance in a range defined by any two of the preceding values.

A solvent may be used to remove portions of the sacrificial coating material 230 in order to expose the individual microwires 211, 211, and 213 to a height 270 near the end portion of the bundle, for example as illustrated in FIG. 2B. Alternatively, the sacrificial coating material may be removed physically, such as by argon sputtering, or chemically such as by plasma etching or acid etching, or by a combination of physical and chemical etching such as reactive ion etching. The difference in etch rates between the sacrificial coating material and microwire components can result in removal of the coating without causing any substantial change to the microwires (e.g. to the mass, configuration and/or spacing of the microwires). The height 270 may correspond to a thickness of the sacrificial coating material 230 that is removed. The height 270 may also correspond to a length of the etched ends of the microwires. In some embodiments, the height 270 may be a distance of less than 50 microns. Alternatively, the height 270 may be 1 micron, 2 microns, 5 microns, 10 microns, 20 microns, 50 microns, 100 microns, 200 microns, 500 microns, or any length within a range defined by any two of the preceding values.

In some embodiments, if the concentricity or shape of the coating material for microwires is changed, the packing of the microwires may be altered as well. For example, referring to the microwire cross-section schematic of FIG. 3A, a round coating 331 added to microwires 311 may create a hexagonal close packed structure. A triangle shaped coating 332 may create an offset pattern of microwires 312, for example as illustrated by the microwire cross-section schematic of FIG. 3B. Such non-circular shapes may be created with an extrusion process for adding additional material. A square shaped material coating 334 around microwires 314 may be used to create a regular square packing structure, for example as illustrated in the microwire cross-section diagram of FIG. 3C. It should be appreciated that various different shapes of the coating material may be used to create a wide variety of different microwire pattern arrangements.

As set forth with reference to FIG. 1C, different sized microwires may be used to create various patterns. Different sized microwires may be combined with additional sacrificial material coatings to create various different patterns for microwire packing. For example, the microwire cross-section diagram of FIG. 3D illustrates a microwire pattern comprising microwires 311 and 313 at different pitches. Many patterns can be created, for example by varying the size of the wires used and/or the size or shape of an additional sacrificial coating added to microwires. The microwire pattern can be modified by adjusting a thickness of the coatings 331/333 surrounding the microwires 311/313. For example, as shown in FIG. 3D, a thickness of the coating 333 may be greater than a thickness of the coating 331, although the disclosure is not limited thereto.

Different sized supplemental wires added to a microwire bundle may or may not be used as electrodes. When different sized wires are not used as electrodes, those wires may be viewed as sacrificial wires that may be eliminated or etched back as needed. One method is to bundle sacrificial wires alongside microwires that are used as microelectrodes to obtain a desired microelectrode pattern, and then remove the sacrificial wires from the bundle. The sacrificial wires may have a material composition such that the sacrificial wires can be removed orthogonally to the microwires. For example, using polymer sacrificial wires along with glass/gold microwires may allow the sacrificial wires to be trimmed using solvents.

In order to control the microwire organization at the distal/microelectrode end, the microwire may be arranged coincident to a flat or complex surface. One method of this arrangement may comprise pressing the microwires onto a previously fabricated flat or complex surface. A flat surface results in a flat arrangement of microwires, capable of electrically accessing a flat plane. A more complex topography, such as one of varying heights may allow a plurality of microelectrodes to access different depths of the brain. A complex surface such as a model of a brain may allow the plurality of microelectrodes to fall at a specific depth relative to the surface of the brain, which may be of highly curved geometry.

4. Microelectrode Embedding and Sealing:

A microwire bundle may be held together and hermetically sealed through the use of infiltrating epoxies or fusible coatings. A low viscosity epoxy or other space filling adhesive material may be introduced into a bound microwire bundle to form a hermetic seal between microwires and join the microwires to one another. Alternatively, a multi-layer coating may be applied as previously described. The multi-layer coating may comprise, for example a thermoplastic material. The thermoplastic material may be melted to seal the microwire bundle together, resulting in a hermetic seal without the need to infiltrate an external epoxy.

For ease of handling, a microwire bundle may be attached to a rigid connector that helps provide stability. One example of a rigid connector is a rigid tube comprised of glass, plastic, or metal that may hold the microwire bundle within it. FIG. 4A illustrates an apparatus 400 showing a side cross-sectional view of a set of microwires 410 held within a rigid tube 430. The microwires may be joined to the rigid fixture by an adhesive, which may act as an embedding agent.

An alternative method of fixing the microwire bundle is by using a mechanical collar 460 to grasp the microwire bundle and fix it in place, which may not require the use of any adhesives. The distal ends of the microwire bundle may spray out, for example as shown in FIG. 4A. Yet another method of holding a microwire bundle together may comprise the use of heat shrink wrap tubing. Heat shrink wrap tubing may be placed around the bundle and shrunk under high temperature to hold a majority of the microwires together. The shrink wrap tubing material may be carefully selected to work well with the microwire materials. For example, glass-insulated gold-core microwires may withstand the high temperatures which may be beneficial for using a PTFE shrink wrap. Other lower coating materials may require a lower temperature shrink wrap tubing material. The heat shrink material may be permanent or temporary, to be removed after the bundle is embedded in adhesive.

Figure 4B:
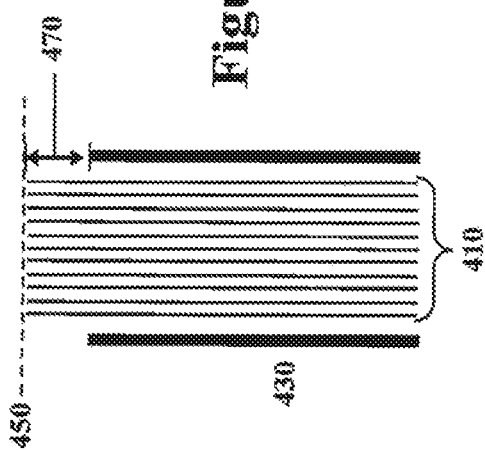
FIG. 4B illustrates an example of a microwire bundle with microwire ends polished flat, in accordance with some embodiments.
Figure 4C:
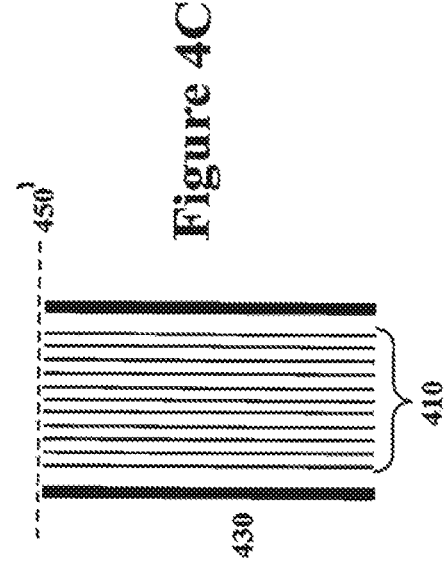
FIG. 4C illustrates an example of a microwire bundle with microwire ends polished flat at the end of the rigid tube, in accordance with some embodiments.

5. Planarizing Microelectrode Bundles:

Planarizing the microwire bundles may be important to help maintain both flatness and smoothness of the distal microwire bundle face; preferably, the microwire bundle face may be flat and smooth in order to successfully mate to a readout electronics chip with high fidelity. To accomplish this, the microwire bundle may be cut and polished in successively finer steps with the first step being a cutting or grinding method to remove the bulk of material on the bundle surface. FIG. 4B illustrates a cross section of microwires 410 in a bundle that have been cut at line or plane 450. The microwire bundle face is subsequently ground against progressively higher grits of polishing pad which may or may not include a colloidal suspension of nanoparticles to achieve an extremely high flatness. The polishing may be carried out using a complex motion such as double-orbital in order to avoid non-uniformity. To support the microwires during the cutting and polishing, it may be preferable to perform the initial cut at line or plane 450 offset by distance 470 from the rigid tube 430 (see FIG. 4B), and subsequent polishing at a lower line or plane 450' near the rigid tube 430 that provide support for the microwires 410 (see FIG. 4C).

The microwires may be polished flat or polished at an angle that is not perpendicular to their longitudinal axis. The polishing angle may be acute or oblique to the longitudinal axis of the microwires. Non-perpendicular polishing may be performed in order to create "angled" or beveled faced microwire bundles that can mate with a flat sensor for off-angle access. Polishing and cutting may be a purely physical/mechanical process, or it may be performed in combination with chemical etching. The amount of material removed during polishing may comprise a microwire length 470 of less than about 10 microns. Alternatively, the amount of material removed may comprise a microwire length of about 10 nm, 20 nm, 50 nm, 100 nm, 200 nm, 500 nm, 1 micron, 2 microns, 5 microns, 10 microns, 20 microns, 50 microns, or a distance within a range defined by any two of the preceding values. In some embodiments, the planarized surface may be flat to within less than 10 microns. In some cases, the surface may be flat to within less than 2 microns. A proximal end of a microwire may typically be flattened. A distal end of a microwire may optionally be flattened to within 30 to 40 microns. In some embodiments, a surface of an end of a microwire may be planarized to within 10 nm, 20 nm, 50 nm, 100 nm, 200 nm, 500 nm, 1 micron, 2 microns, 5 microns, 10 microns, 20 microns, 50 microns, 100 microns, or any distance within a range defined by any two of the preceding values.

6. Microelectrode End Modification:

The microwire end may be modified for a variety of purposes, including biocompatibility, reduced impedance, charge storage, and for facilitating electrical contact. Suitable materials that can be used for modifying the microwire end may include indium, platinum, platinized platinum, or iridium oxide. These materials may have high charge storage and low material-solution interfacial impedance. The microwire tip modification may be asymmetric between different ends of the bundle.

One method for modification of the microwire tip may comprise using physical or chemical vapor deposition of a continuous metal or nonmetal film on the face of a bundle of wires that is embedded in a sacrificial embedding agent or clad in a removable cladding. The sacrificial material outside of the microwires may be stripped, resulting in the removal of the film attached to the removable material. This creates a patterned film on top of each microwire adhering to the microwire face, without any material along the length of the microwire and/or without bridging adjacent microwires together.

If coating is desired along the length of the microwire, the removable embedding material or cladding may be partially removed using methods described previously, for example with respect to FIGS. 2A and 2B before the deposition of the desired material. The subsequent film deposition may coat the exposed length of the wire, and only the deposited film over the sacrificial material may be removed with the sacrificial material.

The deposited material may also be used to facilitate electrical contact with the chip. For example, multilayers of platinum and indium may be deposited on the wire surface, enabling an indium based joint to be formed between chip and wire by improving wetting of solder to the glass microelectrode face. The removal of the sacrificial material may be performed using any of the methods described herein, for example chemical etching, solvent dissolution or gas based etching.

The microwire tip may also be modified by the removal of the cladding material around the metal core. In the example of a glass-coated gold conductor microwire, the glass cladding may be etched to leave an exposed gold core.

Figure 5C:
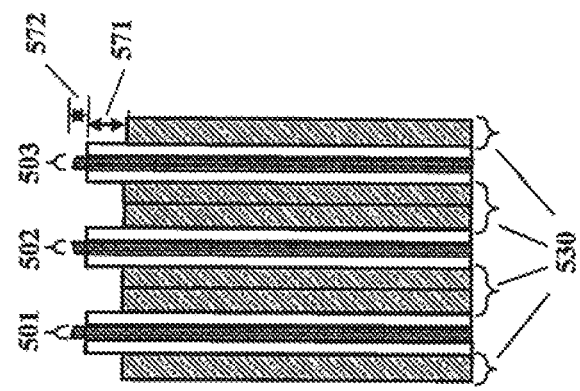
FIG. 5C illustrates the microwire bundle of FIG. 5A with additional conductor material added to the ends of microwires, in accordance with some embodiments.
Figure 5B:
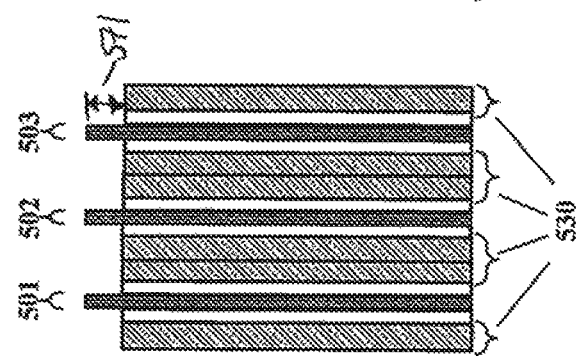
FIG. 5B illustrates the microwire bundle of FIG. 5A with the insulator cladding removed from the ends of microwires, in accordance with some embodiments.
Figure 5A:
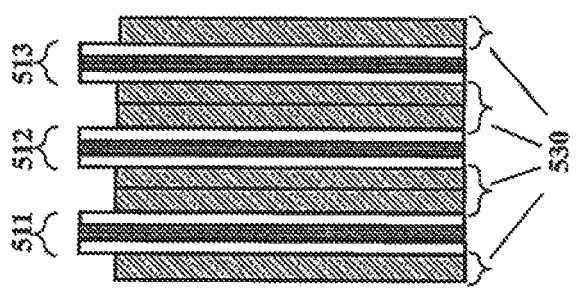
FIG. 5A illustrates a microwire bundle held together with sacrificial material, in accordance with some embodiments.

The end surface of the microwires 511, 512, and 513 for the proximal/readout end may be substantially flat such that the metal electrode cores 501, 502, and 503 of the respective wires are coplanar with the outer insulating layer (e.g. glass cladding), for example as illustrated in FIG. 5A. Sacrificial coating material 530 can be added to provide additional spacing between microwires 511, 512, and 513 similar to other embodiments described herein. Alternatively, the microwire cores 501, 502, and 503 may protrude from the surface of the microwire bundle by a distance 571, for example as illustrated in FIG. 5B. This may be used to sample regions of sub-surface tissue if the bulk of the microelectrodes remains insulated. In the example where the microelectrode insulation is stripped as well (FIG. 5B), this may be used to increase the electrode interface area and lower its impedance, thereby allowing for the electrode to deliver greater charge for stimulation purposes and reduce noise in recording.

Protrusion of the conductive microwire core as illustrated in FIG. 5B may be accomplished by etching away the microwire insulation. For example, with a gold-core glass-insulator microwire this may be accomplished by etching the glass insulator with hydrofluoric acid. Alternatively, the protrusion may be achieved via electroplating on the gold microwires. Protrusion of the entire microwire above the embedded surface may be achieved by etching of the embedding material to recess the material, such as by using oxygen plasma. The microwire core may protrude by a distance 571 which may be less than 50 microns. Alternatively, the distance may be 1 micron, 2 microns, 5 microns, 10 microns, 20 microns, 50 microns, 100 microns, 200 microns, 500 microns, or any length within a range defined by any two of the preceding values.

Post microwire bundle assembly modification to the microwire surface may aid connectorization or may impart some activity to the wires. An example may comprise etching the glass cladding (e.g. outer insulating layer) of the microwire to expose a desired length of gold core, for example as illustrated in FIG. 5B. This creates a larger length of conductive core that may be connectorized to a readout integrated circuit for a microwire bundle. The larger length may aid in connectorization to bond pads on a wafer, which may be silicon.

Alternatively, the conductive core of the wires may be increased in length. For example, an additive process such as electroplating through the conductive core may be used to add additional conductive material to the microwire core to a distance 572, for example as illustrated in FIG. 5C. The microwire core may protrude or extend out from the insulating layer by the distance 572. The microwire core may be increased in length by a distance 572 which may be less than 10 microns. Alternatively, the microwire core may be increased in length by 10 nm, 20 nm, 50 nm, 100 nm, 200 nm, 500 nm, 1 micron, 2 microns, 5 microns, 10 microns, 20 microns, 50 microns, or a distance within a range defined by any two of the preceding values.

Figure 6A:
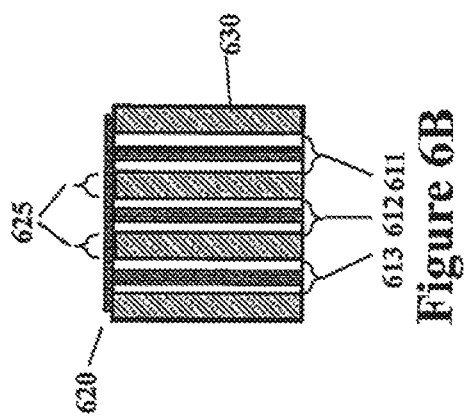
FIG. 6A illustrates a microwire bundle held together with sacrificial material in accordance with some embodiments.
Figure 6B:
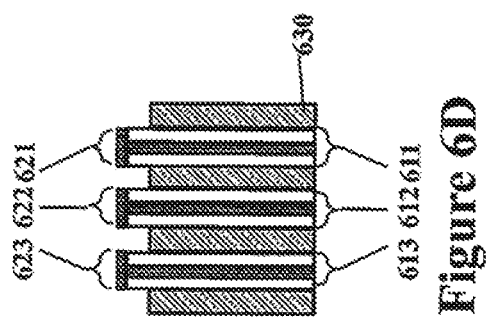
FIG. 6B illustrates the microwire bundle of FIG. 6A with conductor coating added to the end of the microwire bundle, in accordance with some embodiments.
Figure 6C:
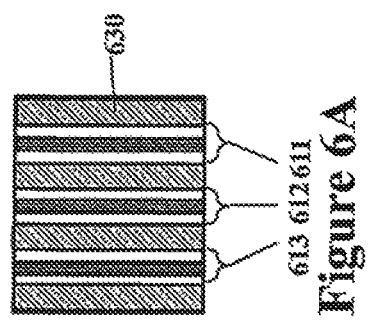
FIG. 6C illustrates the microwire bundle of FIG. 6B with some sacrificial material removed from the end of the microwire bundle, in accordance with some embodiments.
Figure 6D:
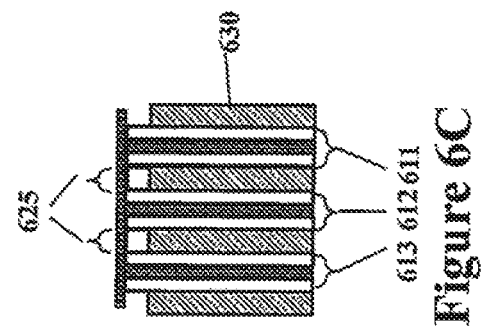
FIG. 6D illustrates the microwire bundle of FIG. 6C after excess conductor coating has flaked away from the end of the microwire bundle, in accordance with some embodiments.

Similar methods may be used to alter the chemical or electrical functionality of the wires. For example, FIG. 6A illustrates a bundle of three microwires 611, 612, and 613 in a bundle that have sacrificial material 630 joining the microwires and spacing them apart. The microwires may comprise an insulating cladding or layer. The exposed end surface of the microwire bundle may comprise a metal layer 620 (e.g. platinum) which may be formed via electroplating deposition or by physical vapor deposition of a conductor material directly onto the microwires or bundle surface, for example as illustrated in FIG. 6B. In the case of a microwire bundle as illustrated in FIG. 6B, it may be beneficial to remove the inter-microwire metal 625 that lies above and between adjacent microwires. To facilitate this goal, some of the sacrificial coating on the outside of the microwires may be stripped near the end of the microwire subsequent to the deposition of metal layer 620, for example as illustrated in FIG. 6C. This may performed with a solvent that soaks through and around the metal layer 620. Once the sacrificial material is removed as illustrated in FIG. 6C, the lack of underlying mechanical support may cause the unsupported inter-microwire metal 625 to flake away and thus effectively pattern the metalized regions to only remain on the microwire end faces 611, 612, and 613, for example as illustrated in FIG. 6D. Accordingly, metal caps 621, 622, and 623 can be formed on the respective end faces of the microwires 611, 612, and 613. The increased size/thickness of the metallized microwire ends (by the metal caps) can help to improve the electrical connection to a readout circuit. Additionally or alternatively, the improved electrical functionality of the microwire may comprise reducing the impedance of the microwire.

7. Microelectrode End Modification:

Microwire end modifications may be performed to obtain specific operation characteristics. For example, the cladding material around the metal core may be changed to obtain certain desired characteristics. FIG. 7A illustrates an end portion of a microwire comprising a metal core 710 and a cladding 730 around the metal core 710. The cladding material 730 may be removed to a distance 771 in a uniform fashion to expose an end segment of the inner metal core 710, as illustrated in FIG. 7B. The cladding material may be removed using exemplary methods and to distances as described elsewhere herein, for example, distance 270 and distance 470 previously described. A large surface area can be created/exposed which may be used as a large surface area electrode if applied to the distal/microelectrode end of the microwire. Alternatively, the exposed metal core of FIG. 7B may create a large electrode contact area when applied to the proximal/readout end, thereby improving contact between the microwire metal core 710 and readout bonding pad (not shown).

The removed cladding material may also be removed in a non-uniform manner that provides other desirable functionality. For example, the cladding material 730 may be removed in a manner that forms a pipette tip structure 791 as illustrated in FIG. 7C. This type of end formation may occur through interfacial etching in a gap between the microwire metal core 710 and cladding material 730. The pipette tip structure 791 may comprise a cone structure. The cone structure 791 allows the metal core 710 to be exposed, while constraining access to the metal core 710 with the surrounding cladding exterior 730.

When the cone structure of FIG. 7C is applied to the distal/microelectrode end, the cone structure can expose a large surface area of the conductor 710 to a small volume of liquid within the tip of the surrounding cladding cone structure 791. This results in localized signal capture with good charge capacity and low impedance at the electrode surface. Furthermore, the pointed shape of the cone structure 791 provides a softer sharpened surface which can reduce damage to tissue during the insertion of the microelectrode.

In some cases, a greater amount of cladding material may be removed to create a recessed pipette structure 792 with an extended metal core 710, for example as illustrated in FIG. 7D. The cone structure of FIG. 7D may be used for both the distal/microelectrode end of a microwire and the proximal/readout end of a microwire.

In the example of FIG. 7D, the cladding material may be removed to a distance of 30 to 50 microns but may optionally be 100 microns. In some embodiments, the cladding material may be removed to a distance of 1 micron, 2 microns, 5 microns, 10 microns, 20 microns, 50 microns, 100 microns, 200 microns, 500 microns, or any length within a range defined by any two of the preceding values.

When the cone structure 792 of FIG. 7D is applied to the distal/microelectrode end, this cone structure may expose a larger surface area of conductor core 710 to a relatively small volume of liquid near the tip of the cone cladding. This may result in a higher charge capacity and lower impedance at the electrode surface while retaining a smaller and more accurate tip location. Furthermore, the extended metal core and recession of the cone structure to a distance 772 can provide a sharpened surface which may reduce the damage to tissue during the insertion of the microelectrode. The tip of the metal core 710 may extended by a distance 772 beyond the tips of the cone structure 792. The distance 772 may be less than 50 microns. Alternatively, the distance 772 may include a distance of 1 microns, 2 microns, 5 microns, 10 microns, 20 microns, 50 microns, 100 microns, 200 microns, 500 microns, or any length within a range defined by any two of the preceding values. In some cases, the tip of the metal core 710 may be further sharpened by cutting the conductor core 710 at an angle as described elsewhere herein.

When the cone structure of FIG. 7D is applied to the proximal/readout end of a microwire, the cone structure 792 of FIG. 7D may constrain the microwire to a defined area where it can bend. In one example, FIG. 7E illustrates the tip of the metal core 710 bent around a tip of the pipette structure 792 when pressed against a contact 770. The contact 770 may comprise a raised or a recessed bond pad. The geometry of the cone structure 792, including the length of the exposed core 710, may be adjusted to increase contact between the core 710 and the pad and/or to prevent shorting. Additionally or alternatively, the geometry of the pad may be adjusted based on the microwire geometry. The arrangement of FIGS. 7D and 7E can increase the length of free microwire core, and can also reduce its stiffness and resistance to buckling. This can allow for a softer, more compliant microelectrode that is constrained in a small area where it may make contact to a readout device. This can help to reduce cross-pad connections between microwire and readout chip.

8. End Modification of Multiclad Microwires:

If a multiclad (and/or a single clad and additionally coated) microwire is used, various structures may be created to provide different features. An intermediate layer between the metal core and outermost coating or cladding may be selectively removed to a controlled depth while leaving the other layers intact. This may create a length of exposed metal core which may be bounded by the outer cladding or coating layers.

FIG. 8A illustrates an exemplary microwire with a multiclad exterior with two layers 830 and 840. The layer 830 corresponds to an inner cladding layer surrounding a conductive core 810, and the layer 840 corresponds to an outer cladding layer surrounding the layer 830. The layer 840 may be a coating layer. If the inner cladding layer 830 is etched back by a distance 871 as shown in FIG. 8B, the proximal/readout surface may mate such that the coating layer 840 controls the degree of contact between the microwire bundle and the readout bond pads. The coating layer 840 may be made of a soft polymer, which may reduce the total contact pressure. The distance 871 may be less than 50 microns. Alternatively, the distance 871 may be 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values.

When applied to the distal/microelectrode end of a microwire, the structure of FIG. 8B may expose a large surface area of conductor to a very small volume of liquid in an area within outer cladding 840. This may provide a localized electrode area with resulting high charge capacity and low impedance at the electrode surface. The size of the exposed fluid region within the outer cladding 840 and the microelectrode core 810 may be controlled by the depth 871 of the inner cladding 830 removed (thus forming the gap shown in FIG. 8B).

Alternatively, both the inner 830 and outer 840 cladding layers may be reduced thus causing more of the metal core 810 to be exposed, for example as illustrated in FIG. 8C. FIG. 8C illustrates an embodiment with the inner layer 830 etched back by a distance 873. The outer layer 840 may be etched back by a distance 872 relative to the tip of the core 810. The etching of the inner layer 830 and outer layer 840 may occur either concurrently, or sequentially. In some cases, the layers 830 and 840 may be etched by back distance 872, and the layer 830 may be further etched back by distance 873. In other cases, the layer 830 may be first etched back by distances 872 and 873, followed by etching back of the layer 840 by distance 872. The layers 830 and 840 may be formed of different materials having different etch selectivity (etch rates) relative to each other. In the example of FIG. 8C, a large amount of metal core 810 may be exposed so that the metal core 810 can be pressed against a bond pad 870 and bent, thus forming a larger contact area for example as illustrated in FIG. 8D. The larger contact area may be desirable for improved electrical contact performance, but may be more likely to bridge adjacent bond pads due to its size. The structure of FIG. 8D may constrain the microwire to a defined area where it may bend, while increasing the length of free metal core 810 and reducing its stiffness and resistance to buckling. This may allow for a softer, more compliant microelectrode that may be constrained to an area where it makes contact, thereby reducing cross-pad connections between microwire and chip. The distances 872 and 873 may be similar or different. For example, the distance 873 may be greater than the distance 872. In some cases, the distance 873 may be less than or equal to the distance 872. Etching back the inner and outer cladding layers 830/840 may be accomplished using any of the methods described previously with respect to FIGS. 2A and 2B, or any of the methods described elsewhere herein.

When the structure of FIG. 8C is applied to the distal/microelectrode end, this structure can expose a larger surface area of metal conductor to an area of liquid near the tip of the microwire. This may result in a higher charge capacity and lower impedance at the electrode surface while retaining a relatively small accurate tip location. Furthermore, the extended metal core may reduce the damage to tissue during the insertion of the microelectrode.

FIG. 8E illustrates an embodiment in which the outer cladding layer 840 is etched back a distance 875 further than the inner cladding layer 830 which may be etched back by a distance 874 relative to the tip of the core 810. The etching of the inner layer 830 and outer layer 840 may occur either concurrently, or sequentially as described elsewhere herein. With the structure of FIG. 8E, the proximal/readout surface may mate such that the inner cladding layer 830 controls the closeness of contact between the bundle and the bond pads. In some embodiments, the inner cladding layer may be made of a hard ceramic, which can provide a relatively higher contact pressure. If the inner cladding layer 830 has been etched back to some degree, but less than the outer cladding layer 840, a sufficient amount of metal core 810 may be exposed so that the metal core can be pressed against the bond pads 870 by the inner cladding layer, forming a small contact area. The small contact area may be desirable for reduced bridging between bond pads, but may have reduced electrical performance due to the smaller contact area. The distances 874 and 875 may be similar or different. Etching back of the inner and outer cladding layers 830/840 may be accomplished by the methods previously described with respect to FIGS. 2A and 2B, or any of the methods described elsewhere herein.

9. Tip Sharpening of Microwires:

To ease insertion of microelectrodes into tissue, the microwires may be formed with sharpened tips. FIG. 9A illustrates a bundle of microwires comprising individual microwires 911, 912, and 913 held together with a sacrificial coating material 930. The sacrificial coating material may be similar to the sacrificial coating materials described elsewhere herein. The microwires may comprise an insulating cladding or layer. To sharpen the tips of the microwires, the end of the microwire bundle may be cut at an angle 971 relative to the surface normal of the wall of the bundle, for example as illustrated in FIG. 9B. Optionally, the microwire bundle may be polished along a cutting plane 921. The microwire bundle as shown may have a beveled cut surface of about 30 degrees. Alternatively, the bundle may be cut at an angle of 1 degree, 2 degrees, 5 degrees, 10 degrees, 20 degrees, 50 degrees, 60 degrees, 70 degrees, 80 degrees, 90 degrees, or any angle within a range between any two of the preceding values.

After cutting at an angle, the microwires may be rearranged such that their tips are substantially within the same plane, in some cases to with 5 microns, for example as illustrated by plane 922 in FIG. 9C. In some embodiments, the tips of the microwires may be substantially within the same plane to within 1 micron, 2 microns, 5 microns, 10 microns, 20 microns, 50 microns, 100 microns, 200 microns, 500 microns, or any distance within a range defined by any two of the preceding values. It is noted that the (proximal/readout) end can also be cut evenly in a manner similar to the above. Next, an inner cladding layer surrounding the metal core may be reduced by a distance 972 and the sacrificial coating layers 930 may be further reduced by a distance 973 to produce the protruded microelectrode ends shown in FIG. 9D, that comprise sharpened microwire ends for easy insertion into tissue. The cladding layer and coating material may be reduced by distances 972 and 973 which may comprise lengths similar to other coating reduction steps described elsewhere herein.

In some microelectrode bundle embodiments, it may be desirable to have microwires with different lengths, such that the tips do not terminate on the same plane, in order to sample different depths of the tissue. Thus, after the cladding and coating reduction stage of FIG. 9D, the microwires may be arranged such that each microwire extends to a different depth, for example as illustrated in FIG. 9E. For example, the tip of microwire 911 may be higher than a base portion of microwire 912 by a distance 974, and the tip of microwire 913 may be higher than the base portion of microwire 912 by a distance 975. The proximal/readout end may also be cut to substantially even out the proximal/readout end. The distances 974 and 975 may be similar or different. For example, in some embodiments, distance 974 may be shorter than distance 975. Distances 974 and/or 975 may comprise a length of less than 500 microns. Alternatively, distances 974 and/or 975 may comprise a length of 10 microns, 20 microns, 50 microns, 100 microns, 200 microns 500 microns, 1 mm, 2 mm, 5 mm, 10 mm or any length within a range defined by any two of the preceding values.

10. Electrochemical End Modification:

Electrochemical modification of the wire bundle may be performed on both the distal and proximal ends of the bundle. Electrochemical modification may comprise tip-shaping of the wires to form sharp tips and/or low impedance tips. The electrochemical modification may be additive or subtractive with respect to how the material may be modified. The following electrochemical modification methods according to various embodiments of the disclosure can be applied to large-scale bundles of microelectrodes, in contrast to conventional electrochemical modification techniques that are typically applied for only single wires. The electrochemical modification methods in the present disclosure can include applying electrical potential or current to a highly parallelized bundle of microelectrodes, as described in further detail with reference to FIGS. 10A through 16C.

Electrochemical modification can be carried out in an electrically conductive bath. In the case of subtractive electrochemical modification, the bath may contain reactive elements such as sodium or potassium hydroxide, at a concentration above 0.01M and below 10M. The bath may also contain acids such as sulfuric or phosphoric acid. The subtractive process may be performed under an applied voltage at the metal core, which may typically be positive. The specific formulation used in the bath can vary depending on the selected material, as known to those skilled in the art.

Subtractive modification may result in two types of general geometries: (1) smooth and flat material removal (often called electropolishing), or (2) the sharpening of the wire to an apex (called electrosharpening). The geometries may depend on factors such as mass transport of chemical reagents to the material surface, applied potential at the electrode surface, solution composition, temperature, applied forces to the electrode during the process, and the like.

The additive process may be carried out using a solution that contains the dissolved ions of the material. An electric potential may be applied to the electrode which is undergoing modification, but this may not be necessary. When a potential is applied, it may typically be negative, which causes the dissolved ions to reduce onto the surface of the material as a solid. When a potential is not applied to the electrode undergoing modification, a reducing agent may typically be included in the solution to enable the application of the material coating. Growth of material at the surface of the electrode may take on different forms and morphologies depending on the deposition conditions, including reagent chemistry, chemical mass transport, temperature, electric potential applied to the electrode, and the like.

In large microelectrode bundles which may be used for neural recording, one of the challenges faced may be difficulty in achieving penetration into the tissue. It may therefore be desirable to sharpen the tips of each electrode in a bundle array, and to reduce the bulk microelectrode force at the distal, brain facing end of the bundle. For a clad or coated microwire such as those bundles may be comprised of, a first step may be to planarize the microelectrode bundle or otherwise polish it into the desirable shape. However, the cross sectional surface of the wire may be exposed to some degree. FIG. 10A shows a microwire conductive core 1010 with a coating 1030. Subsequently, as shown in FIG. 10B, the coating 1030 may be etched to a distance 1071 to expose a length of conductive wire. This etch may be carried out either chemically or through reactive ion etching, laser ablation, exposure of a photoreactive polymer or any other method. For example, a wire may be exposed to a length of 20 um. Alternatively, the wire may be exposed to a distance 1071 of 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values.

Subsequently, the conductive wire material may be subtractively removed using the "electrosharpening" or the "electropolishing" methods described herein to create the desired geometry. The sharpened wire may either be above the surface of the coating, as shown in FIG. 10C or if desired, it may be recessed to a distance 1172, as shown in FIG. 11C. The sharpened wire may comprise an apex 1091 (FIG. 10C) or apex 1192 (FIGS. 11C and 11D). The wire may be sharpened such that the diameter of a tip of the wire may be less than 500 nm. In some embodiments, the diameter of a tip may be atomically thin. In some embodiments the diameter of the tip of the wire may be 0.1 nm, 0.2 nm, 0.5 nm, 1 nm, 2, nm 5 nm, 10 nm, 20 nm, 50 nm, 100 nm, 200 nm, 500 nm, 1 micron, 2 microns, 5 microns or any diameter within a range defined by any two of the preceding values.

Figure 11B:
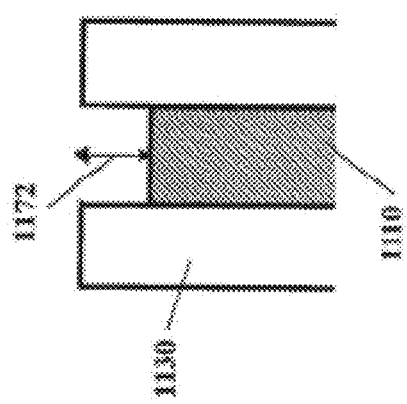
FIG. 11B illustrates the end of the microwire of FIG. 11A after wire material has been subtractively removed, in accordance with some embodiments.
Figure 11D:
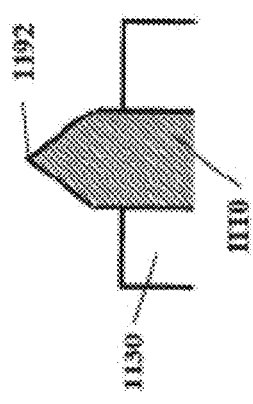
FIG. 11D illustrates the end of the microwire of FIG. 11C after the coating has been etched, in accordance with some embodiments.
Figure 11A:
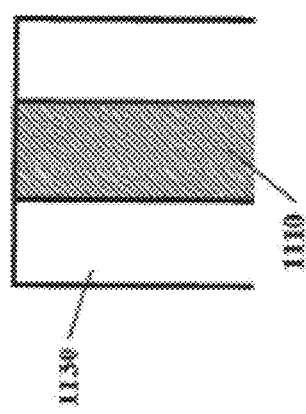
FIG. 11A illustrates the end of a microwire which may be electropolished or electrosharpened, in accordance with some embodiments.
Figure 11C:
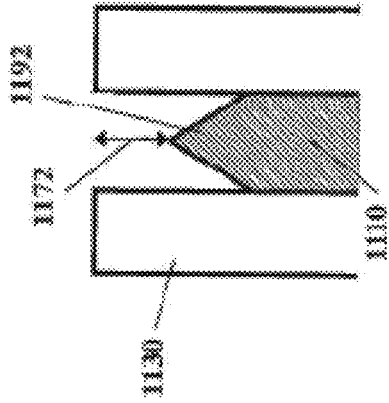
FIG. 11C illustrates the end of the microwire of FIG. 11B after the wire has been sharpened, in accordance with some embodiments.

An alternative method for creating an electrosharpened tip is shown in FIGS. 11A to 11D. FIG. 11A shows a microwire conductive core 1110 with a coating 1130. Subsequently, as shown in FIG. 11B, the core 1110 may be etched to a distance 1172. The wire 1110 may be below the surface of the coating 1130 by a distance 1172 which may be less than 50 microns. Alternatively, the wire may be below the surface of the coating 1130 by a distance of 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values. If the wire is electropolished, then a flat surface may be created. FIG. 11B shows the result of electro polishing for a sufficient time to produce a flat microwire recessed surface. FIG. 11C shows the microwire of FIG. 11B after an electrosharpening step to form a sharpened tip 1192. Subsequently, as shown in FIG. 11D, a portion of the coating 1130 may be removed and the rest of the preparation of the distal end of the wire may continue, such as removal of the sacrificial coating layer to fully expose the sharpened wire tip 1192.

Figure 12A:
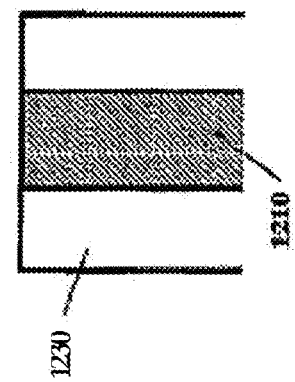
FIG. 12A illustrates the end of the microwire which may be lengthened by electrodeposition, in accordance with some embodiments.
Figure 12B:
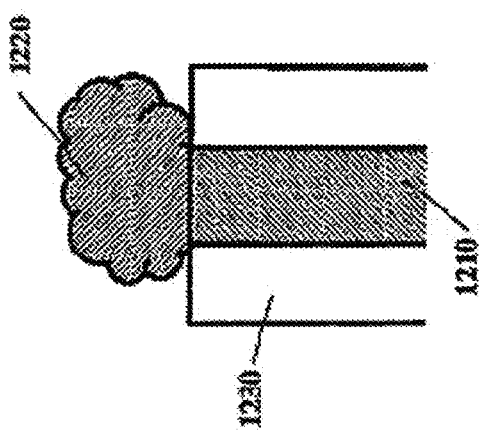
FIG. 12B illustrates the end of the microwire of FIG. 12A after material has been electrodeposited, in accordance with some embodiments.
Figure 12C:
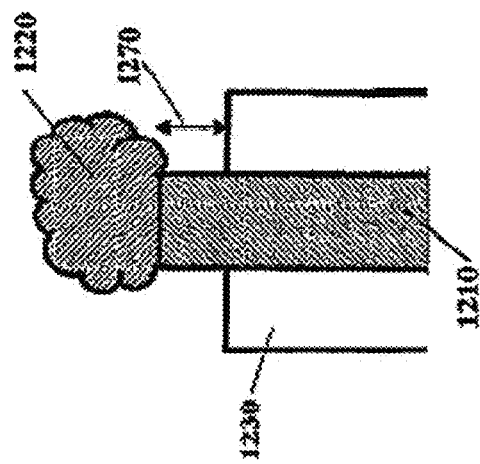
FIG. 12C illustrates the end of the microwire of FIG. 12B after coating material has been removed, in accordance with some embodiments.

Alternately, electrodeposition may be carried out. This may be useful at both the distal and proximal ends of a wire or a microwire bundle. At the proximal end, this technique may be used to increase the surface area and bondability of the microwire bundle against the readout integrated circuit. This may be seen in FIGS. 12A to 12C. Referring to FIG. 12A, a flat microwire conductive core 1210 with a coating 1230 is provided. An exposed tip of the conductive core 1210 may have a second material 1220 electrodeposited on it. As shown in FIG. 12B, the second material 1220 may be electrodeposited such that the material rises above the coating plane and facilitates bonding to a readout circuit. The addition of the second material may also increase the wettability of the bonding metal or act as the bonding filler itself. As shown in FIG. 12C after electrodeposition, the coating 1230 may be recessed by a distance 1270 to increase the bonding area at the end portion of the conductive core 1210. The coating may be recessed to a distance of less than 100 microns. Alternatively, the coating may be recessed by 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values.

Figure 13A:
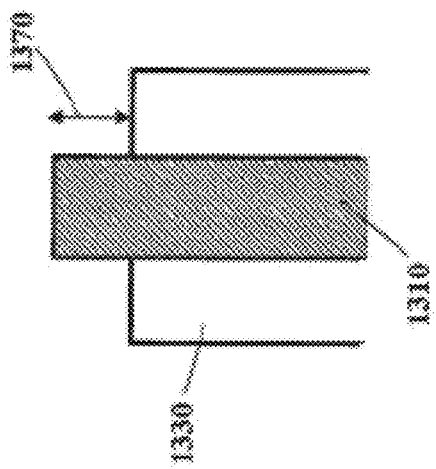
FIG. 13A illustrates the end of a coated microwire on which an electroplated film may be applied, in accordance with some embodiments.
Figure 13B:
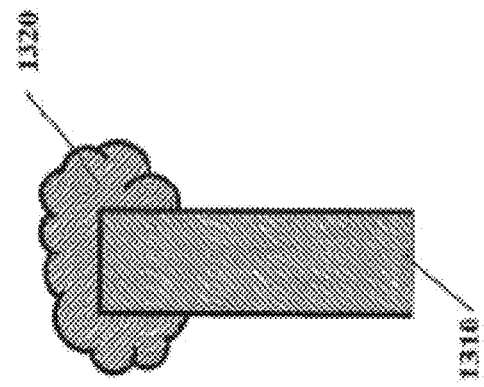
FIG. 13B illustrates the end of the coated microwire of FIG. 13A after coating material has been removed, in accordance with some embodiments.

At the distal end, additive electrodeposition may alter the exposed tissue-facing material, provide hermetic sealing, change the tissue response, or decrease the electrode impedance of the exposed conductive core. For example, FIG. 13A shows a coated microwire comprising a conductive core 1310 and a coating 1330. Referring to FIG. 13B, the coating 1330 may be etched back to a distance 1370. The coating 1330 may be etched back to a distance of less than 100 microns. Alternatively, the coating 1330 may be etched back to a distance of 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values.

Figure 13C:
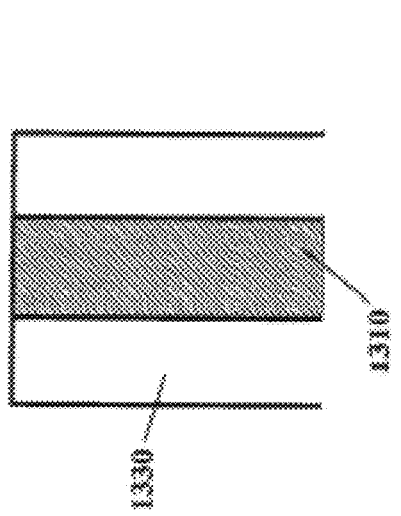
FIG. 13C illustrates the end of the coated microwire of FIG. 13B after an electroplated film is applied, in accordance with some embodiments.
Figure 13D:
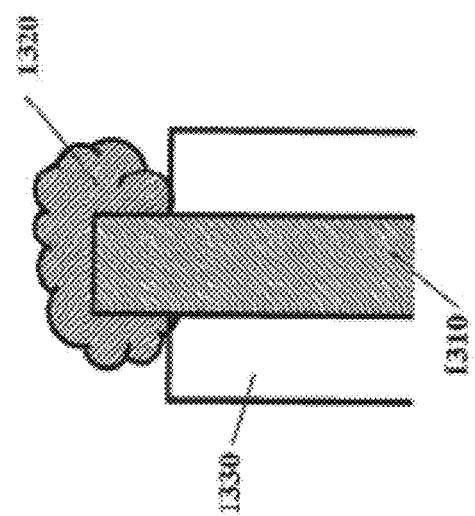
FIG. 13D illustrates the end of the coated microwire of FIG. 13C after cladding material has been removed, in accordance with some embodiments.

As shown in FIG. 13C, an electroplated film 1320 may be applied. At this stage, if the film were made around the coating, then a hermetic seal may be created by gap-filling exposed areas of solution with the electrodeposited material 1320. The electrode material which may be electrodeposited may also alter the tissue material—for example, inert metals such as gold or platinum may be electrodeposited on less biocompatible materials to decrease the tissue toxicity. Optionally, as shown in FIG. 13D, the coating 1330 may be removed. In some cases, the electrodeposited material may also reduce the electrode impedance even if the coating is removed. For example, in a first case, the second material may naturally be of lower electrochemical impedance, such as through the deposition of iridium oxide onto stainless steel electrodes. In a second case, both materials may be chemically identical (Platinum on platinum); however, through control of the electrodeposition parameters such as potential and chemical composition, the as-deposited material may have a rough surface, which increases the surface area of the electrode for the same volume.

Figure 14C:
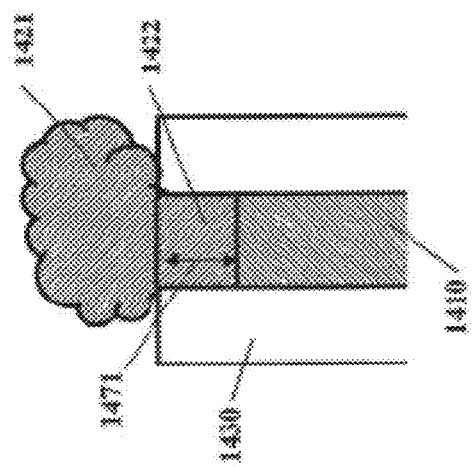
FIG. 14C illustrates the end of the microwire of FIG. 14B after material has been deposited upon the recessed microwire, in accordance with some embodiments.
Figure 14F:
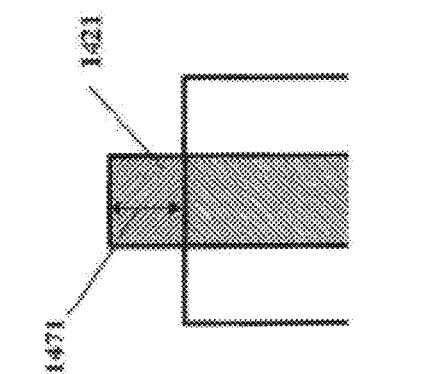
FIG. 14F illustrates the end of the microwire of FIG. 14E after an electrosharpening step, in accordance with some embodiments.
Figure 14B:
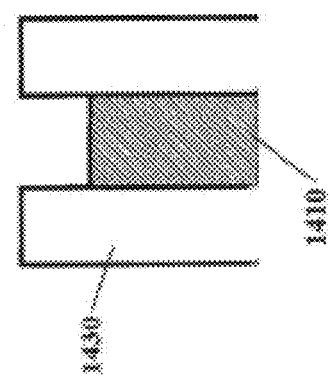
FIG. 14B illustrates the end of the microwire of FIG. 14A after an electropolishing step, in accordance with some embodiments.
Figure 14E:
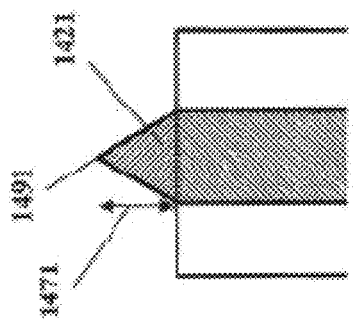
FIG. 14E illustrates the end of the microwire of FIG. 14D after insulation has been recessed, in accordance with some embodiments.
Figure 14A:
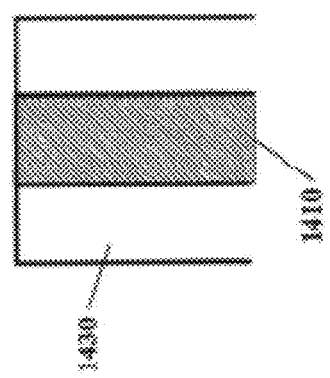
FIG. 14A illustrates the end of a microwire which may be both electropolished and electroplated, in accordance with some embodiments.
Figure 14D:
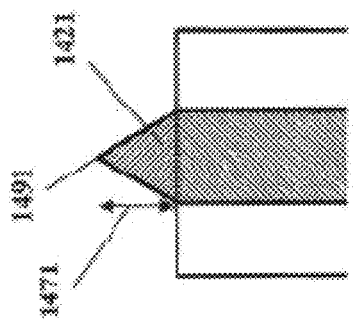
FIG. 14D illustrates the end of the microwire of FIG. 14C after excess material has been removed, in accordance with some embodiments.

Another method as shown in FIGS. 14A-14F may integrate both techniques together sequentially. For example, electropolishing may first be conducted, followed by electrodeposition in order to create a "tip" of a different material on the microelectrode. As shown in FIG. 14A, first, a microwire comprising a conductive core 1410 and an insulating cladding 1430 may be prepared. Subsequently, as shown in FIG. 14B, an electropolishing step may be conducted to recess the conductive core 1410 into the insulation layer 1430 by a distance 1471, with a depth equal to the desired "tip" length. As shown in FIG. 14C, a second desirable material to form the tip may be deposited within the recessed microwire. The second material may comprise a first portion 1422 within the recessed region and a second portion 1421 above the cladding layer 1430. The second material may be more conductive than the first conductive material 1410 to enable either electrical recording or stimulation of neural signals (having a low impedance or high charge capacity). The second material may comprise, for example tungsten which can be shaped to form a sharp tip in subsequent processing steps. Optionally, as shown in FIG. 14D, excess second material may be removed or planarized by a process such as mechanical polishing, electropolishing, or chemical etching. Afterwards, as shown in FIG. 14E, the insulation cladding 1430 may optionally be recessed to a distance 1471 to expose part or all or part of the second electrodeposited material 1421. The distance 1471 may be less than 100 microns. Alternatively, the distance 1471 may be 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values. As shown in FIG. 14F, the second material 1421 may then be electrosharpened in order to form a sharp tip 1491, which may not be capable of being formed with the first material 1410 alone.

Figure 15C:
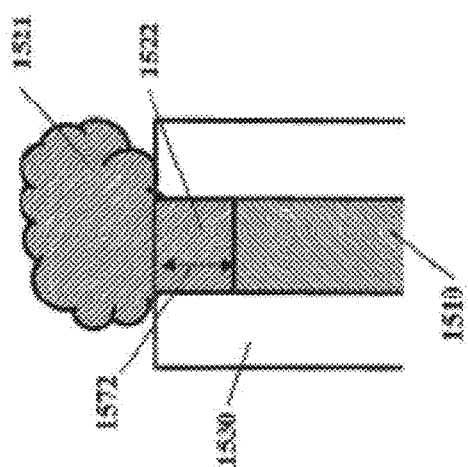
FIG. 15C illustrates the end of the microwire of FIG. 15B after material has been deposited upon the recessed microwire, in accordance with some embodiments.
Figure 15F:
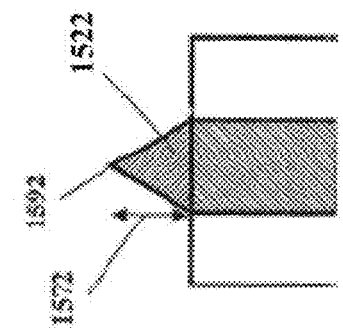
FIG. 15F illustrates the end of the microwire of FIG. 15E after coating has been removed, in accordance with some embodiments.
Figure 15B:
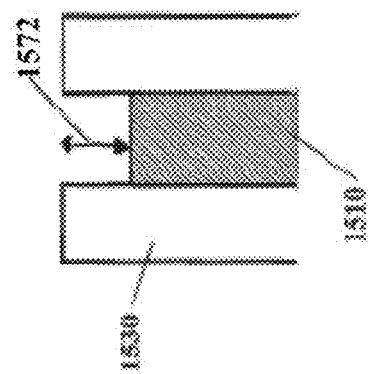
FIG. 15B illustrates the end of the microwire of FIG. 15A after an electropolishing step, in accordance with some embodiments.
Figure 15E:
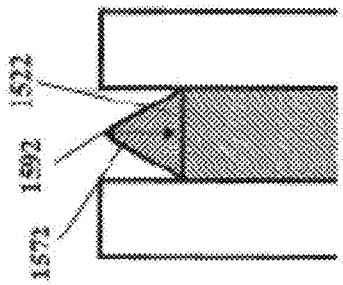
FIG. 15E illustrates the end of the microwire of FIG. 15D after an electrosharpening step, in accordance with some embodiments.
Figure 15A:
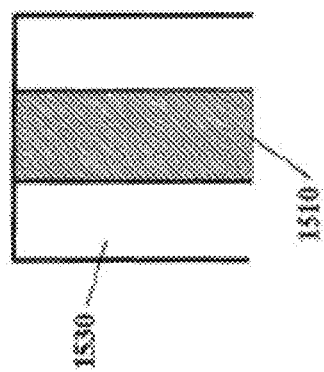
FIG. 15A illustrates the end of a microwire which may be both electropolished and electroplated, in accordance with some embodiments.
Figure 15D:
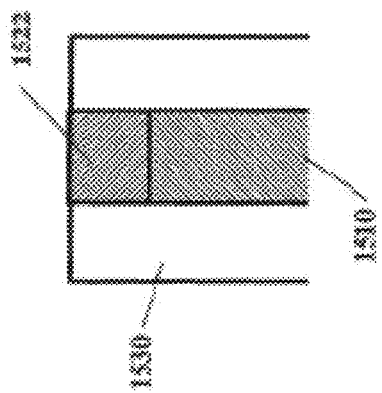
FIG. 15D illustrates the end of the microwire of FIG. 15C after excess material has been removed, in accordance with some embodiments.

An alternative method is shown in FIGS. 15A-15F. As shown in FIG. 15A, first, a microwire comprising a conductive core 1510 and an insulating cladding 1530 may be prepared. Subsequently, as shown in FIG. 15B, an electropolishing step may be conducted to recess the conductive core 1510 into the insulation layer 1530 by a distance 1572, with a depth equal to the desired "tip" length. As shown in FIG. 15C, a second desirable material to form the tip with may be deposited within the recessed microwire. The second material may comprise a first portion 1522 within the recessed region and a second portion 1521 above the cladding layer 1530. The second material may be more conductive than the first conductive material 1510 to enable either electrical recording or stimulation of neural signals (having a low impedance or high charge capacity). The second material may comprise, for example tungsten which may be shaped to form a sharp tip in subsequent processing steps. Optionally, as shown in FIG. 15D, excess second material may be removed or planarized by a process such as mechanical polishing, electropolishing, or chemical etching. As shown in FIG. 15E, the second material 1522 may be electrosharpened in order to form a sharp tip 1592, which may not be capable of being formed with the first material 1510 alone. As shown in FIG. 15F, if the insulation 1530 was not originally removed, then it may be etched or removed down by a distance 1572 to expose the sharpened tip 1592. The distance 1572 may be formed using any of the methods disclosed herein to a distance which may be less than 50 microns. Alternatively, the distance 1572 may be 100 nm, 200 nm, 500 nm, 1 micron, 2 microns, 5 microns, 10 microns, 20 microns, 50 microns, 100 microns, 200 microns 500 microns, 1 mm, 2 mm, 5 mm, 10 mm or any length within a range defined by any two of the preceding values.

Any of the aforementioned techniques, for example those described with respect to FIGS. 10A-15F, may be carried out on bundles of homogenous or heterogeneous microwires of more than 100 microwires, which differs from conventional electromodification techniques that are typically performed on single electrodes at a given time. Alternatively, the techniques described herein may be carried out on bundles of microwires comprising 2, 5, 10, 20, 50, 100, 200, 500, 1000, 2000, 5000, 10000, 20000, 50000, 10000, 100000, 1000000, 10000000 or any number of microwires within a range defined by any two of the preceding values. The systems in the present disclosure can utilize the methods described herein on parallel bundles of microelectrodes, which is often useful since large bundles of more than 100 microwires, especially in the range of more than 1000 microwires or microelectrodes, can be efficiently modified thereby reducing processing time, and can also allow for electrode modification post device assembly (instead of pre-device assembly).

Figure 16A:
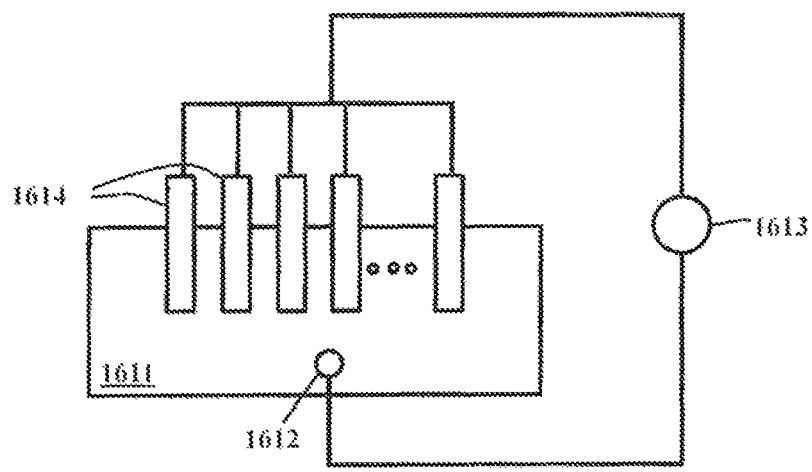
FIG. 16A shows a circuit for electropolishing and/or electrosharpening comprising a bundle of microwires that have been shorted together, in accordance with some embodiments.
Figure 16B:
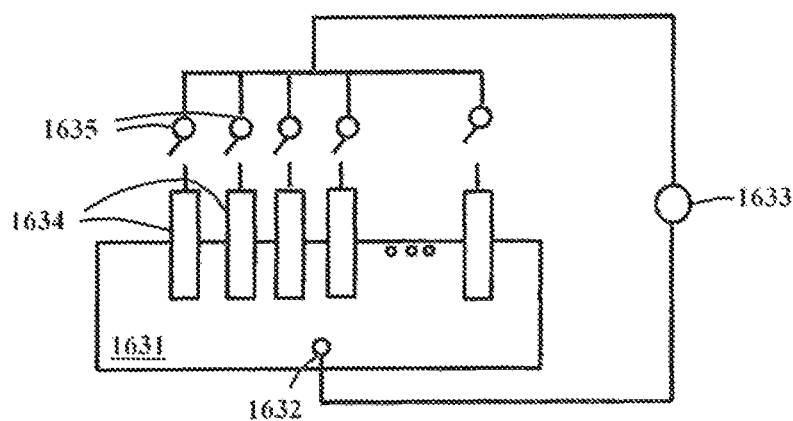
FIG. 16B shows a switchable circuit for electropolishing and/or electrosharpening comprising a bundle of microwires with the switches in an "off" position, in accordance with some embodiments.
Figure 16C:
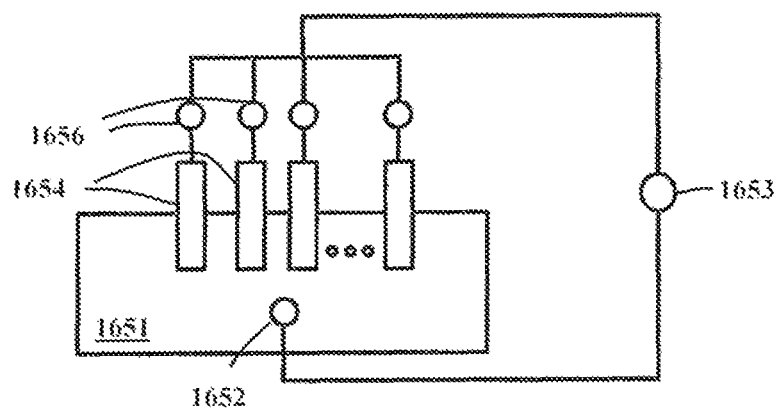
FIG. 16C shows a circuit for electropolishing and/or electrosharpening comprising a bundle of microwires with the switches in an "on" position, in accordance with some embodiments.

FIGS. 16A to 16C show exemplary systems for electropolishing and/or electroshaping. A first system is shown in FIG. 16A. The embodiment of FIG. 16A shows an electrochemical bath 1611 comprising a counter electrode 1612 connected to a voltage or current source 1613 and to an electrode bundle comprising a plurality of electrodes 1614. The electrode bundle comprising electrodes 1614 may be first shorted together on an end which does not undergo modification. This may be performed using a variety of methods, and two examples are described as follows. In a first example, the cladding on the electrodes may be removed by etching, either plasma or chemical depending on the cladding material. After exposing a small amount of wire (for example, greater than 20 microns), a conductive paste may be applied to the backside of the bundle to short all or a plurality of the microelectrodes together. In a second example, the bundle may simply have some of the metal core exposed, for example through polishing of the back of the backside of the bundle which may not remove the cladding. A conductive contact agent may then be applied. The agent may be a conductive epoxy, conductive paste, physical or chemical vapor deposited metal, solder, or liquid metal. It may be useful for the agent to have in some part a particle or grain size smaller than the exposed area of the bundle. Once the bundle of microelectrodes are shorted together, a single voltage or current source 1613 may be applied to the backside of the bundle, and all or a plurality of the electrodes may be electrochemically modified in parallel. Current and voltage measurement of the bundle during the process may be useful in this embodiment as to inform a threshold for process completion. For example, in the case of electrosharpening, current monitoring may be used to inform a user when the process is complete.

A second exemplary system is shown in FIG. 16B. The embodiment of FIG. 16B shows an electrochemical bath 1631 comprising a counter electrode 1632 connected to a voltage or current source 1633 and to an electrode bundle comprising a plurality of microelectrodes 1634. The microelectrode bundle may be coupled to an integrated circuit or planar microelectrode array using any of the previously described methods. In this configuration, each wire core may touch on a single "pixel" 1635 of the underlying circuit. In these circuits, each individual circuit may be a voltage or current source and may not have the capability to readout the associated voltage or current through each microelectrode. For example, such a circuit may comprise a micro-display circuit which outputs a constant but controllable voltage on each pixel without current feedback. The array may also comprise a pixel array containing switches, which controls the passing of current or application of voltage from a single source. In order to implement threshold current for individual wire control, a single current measurement unit may be applied at the counter-electrode. The electrochemical modification of each electrode may be performed sequentially, using the current readout capability at the counter electrode to control the electrodeposition of each channel as it is activated. The modification of the microelectrodes may also be performed in parallel. For example, small patterns of microelectrodes may be modified to improve consistency or generate patterns, or a pulsed deposition method may be used. In the pulsed method, each pixel may be driven with a short pulse one-after another. This method allows for high uniformity in pulsing performance because the "off" time of each electrode may be used to pulse another electrode "on". Short pulse "on" times and longer "off" may lead to superior performance as the local bath around each electrode returns to equilibrium during the "off" period.

A third exemplary system is shown in FIG. 16C. The embodiment of FIG. 16C shows an electrochemical bath 1651 comprising a counter electrode 1652 connected to a voltage or current source 1653 and to an electrode bundle comprising s plurality of electrodes 1654. The system of FIG. 16C may be similar to the system of FIG. 16B, with the exception that the pixels each may contain a current measurement circuit 1656 which is no longer present at the counter-electrode. The system of FIG. 16C may provide all or some of the advantages of the system of FIG. 16B, with the ability to electrochemically modify all or some of the electrodes in parallel. It may still be desirable to do patterned or sub-section modification in this method, in order to generate functionally heterogeneous patterns or to manipulate the local chemical gradient around the electrodes during electrochemical modification.

It is understood that FIGS. 16A-16C are examples of electropolishing and/or electroshaping systems according to embodiments of the present disclosure. Any of the systems of FIGS. 16A to 16C can be used to either electroshape or electropolish an electrode bundle comprising microelectrodes. Alternatively, any of the systems of FIGS. 16A to 16C can be used to both electroshape and electropolish an electrode bundle comprising microelectrodes. Variations to the electropolishing and/or electroshaping systems may be known to one of skill in the art.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosures. It should be understood that various alternatives to the embodiments described herein may be employed. It is intended that the following claims define the scope of the invention and that methods and structures within the scope of these claims and their equivalents be covered thereby.

What is claimed is:

1. A method for forming a bundle of microelectrodes, comprising:
    coating a microwire comprising a first cladding layer with a second cladding layer to form a multiclad microwire;
    wrapping the multiclad microwire repeatedly around a spool;
    cutting the multiclad microwire on the spool to form a stack of cut multiclad microwires;
    securing the stack of cut multiclad microwires together to form the bundle of microelectrodes; and
    removing a portion of the first cladding layer at a first end of the stack of cut multiclad microwires to expose an electrical conductor at the first end of the stack.

2. The method of claim 1, further comprising:
    removing a portion of the second cladding layer at the first end of the stack of cut multiclad microwires.

3. The method of claim 1, wherein removing the portion of the first cladding layer results in a conical pipette geometry due to differential etching between the electrical conductor and the first cladding layer.

4. The method of claim 1, wherein selective removal of the first cladding layer and an embedding material allows the electrical conductor to be exposed, and the exposed electrical conductors on proximal ends of the microwires are used for bonding to readout electronics, and the exposed electrical conductors on distal ends of the microwires are used as large surface area electrodes for tissue penetration.

5. The method of claim 1, wherein selective etching of the first cladding layer results in a conical pipette geometry due to differential etching at an interface between the electrical conductor and the first cladding layer.

6. The method of claim 1, wherein removal of a portion of the second cladding layer exposes the first cladding layer as a primary contact surface.

7. The method of claim 1, wherein removal of a portion of the first cladding layer exposes the second cladding layer as a primary contact surface.

* * * * *